United States Patent
Lee et al.

(10) Patent No.: US 11,602,581 B2
(45) Date of Patent: Mar. 14, 2023

(54) CELL-ENCAPSULATED HYDROGEL BLOCK PREPARATION FOR 3D BIOPRINTING-BASED TISSUE ENGINEERING AND MACROSTRUCTURE ASSEMBLY TECHNOLOGY THEREOF

(71) Applicant: INDUSTRY-UNIVERSITY COOPERATION FOUNDATION HANYANG UNIVERSITY, Seoul (KR)

(72) Inventors: Dong Yun Lee, Seoul (KR); Seon Jae Lee, Seoul (KR)

(73) Assignee: INDUSTRY-UNIVERSITY COOPERATION FOUNDATION HANYANG UNIVERSITY, Seoul (KR)

( * ) Notice: Subject to any disclaimer, the term of this patent is extended or adjusted under 35 U.S.C. 154(b) by 264 days.

(21) Appl. No.: 16/651,068

(22) PCT Filed: Sep. 27, 2018

(86) PCT No.: PCT/KR2018/011420
§ 371 (c)(1),
(2) Date: Mar. 26, 2020

(87) PCT Pub. No.: WO2019/066488
PCT Pub. Date: Apr. 4, 2019

(65) Prior Publication Data
US 2020/0222592 A1   Jul. 16, 2020

(30) Foreign Application Priority Data
Sep. 27, 2017 (KR) .......... 10-2017-0124934

(51) Int. Cl.
| | | |
|---|---|---|
| A61L 27/52 | (2006.01) | |
| A61L 27/20 | (2006.01) | |
| A61L 27/22 | (2006.01) | |
| A61L 27/24 | (2006.01) | |
| A61L 27/56 | (2006.01) | |
| A61L 27/38 | (2006.01) | |
| B33Y 70/00 | (2020.01) | |
| A61L 27/26 | (2006.01) | |
| B33Y 10/00 | (2015.01) | |
| B33Y 80/00 | (2015.01) | |
| A61L 27/44 | (2006.01) | |
| A61L 27/58 | (2006.01) | |
| C08L 5/04 | (2006.01) | |

(52) U.S. Cl.
CPC .............. *A61L 27/52* (2013.01); *A61L 27/20* (2013.01); *A61L 27/227* (2013.01); *A61L 27/24* (2013.01); *A61L 27/38* (2013.01); *A61L 27/56* (2013.01); *B33Y 70/00* (2014.12)

(58) Field of Classification Search
CPC ................................................ A61K 47/6903
See application file for complete search history.

(56) References Cited

U.S. PATENT DOCUMENTS

| | | | |
|---|---|---|---|
| 6,143,293 A | 11/2000 | Weiss et al. | |
| 2013/0085571 A1* | 4/2013 | Mueller | .............. A61L 27/3813 |
| | | | 600/36 |
| 2015/0051148 A1 | 2/2015 | Cohen et al. | |
| 2017/0216498 A1* | 8/2017 | Kang | ...................... A61L 27/20 |

FOREIGN PATENT DOCUMENTS

| | | |
|---|---|---|
| JP | 2015-107645 A | 6/2015 |
| KR | 10-2013-0130714 A | 12/2013 |
| KR | 10-2015-0097087 A | 8/2015 |
| KR | 10-1630617 B1 | 6/2016 |
| KR | 10-2016-0096829 A | 8/2016 |
| WO | 2012/048165 A2 | 4/2012 |

OTHER PUBLICATIONS

Zhang et al. (2016) Biodegradable scaffold with built-in vasculature fororgan-on-a-chip engineering and direct surgical anastomosisNature materials, vol. 15, pp. 669-678.*
Communication dated Mar. 31, 2020, issued by the Korean Intellectual Property Office in application No. 10-2018-0115084.
Chang Mo Hwang et al., "Fabrication of three=dimensional porous cell-laden hydrogel fortissue engineering", Biofabrication, 2010, p. 035003, vol. 2.
International Search Report for PCT/KR2018/011420 dated Mar. 26, 2019 [PCT/ISA/210].

* cited by examiner

*Primary Examiner* — Suzanne M Noakes
*Assistant Examiner* — Jae W Lee
(74) *Attorney, Agent, or Firm* — Sughrue Mion, PLLC

(57) ABSTRACT

A three-dimensional hydrogel scaffold of the present invention contains a cell to be transplanted in vivo and comprises a first hydrogel block on which a plurality of holes are formed and one or more second hydrogel blocks which are assembled to the holes and are biodegradable. A large hydrogel scaffold can be prepared by means of the assembly of the blocks. The survivability of the cell being transplanted is high and the biodegradability of the blocks varies, and thus the risk of hypoxia is reduced.

11 Claims, 39 Drawing Sheets

[UNASSEMBLED CONSTRUCT]

[BLOCK A]

[BLOCK B]

[ASSEMBLED CONSTRUCT]

[UNASSEMBLED CONSTRUCT]

[BLOCK A]

[BLOCK B]

[ASSEMBLED CONSTRUCT]

[UNASSEMBLED CONSTRUCT]

[BLOCK A]

[UNASSEMBLED CONSTRUCT]

[BLOCK A]

[ASSEMBLED CONSTRUCT]

CELL-ENCAPSULATED HYDROGEL BLOCK PREPARATION FOR 3D BIOPRINTING-BASED TISSUE ENGINEERING AND MACROSTRUCTURE ASSEMBLY TECHNOLOGY THEREOF

CROSS REFERENCE TO RELATED APPLICATIONS

This application is a National Stage of International Application No. PCT/KR2018/011420 filed Sep. 27, 2018, claiming priority based on Korean Patent Application No. 10-2017-0124934 filed Sep. 27, 2017.

TECHNICAL FIELD

The present invention relates to technology of forming a cell-encapsulating hydrogel block for three-dimensional (3D) bioprinting-based tissue engineering and assembling a macrostructure thereof.

BACKGROUND ART

Around the world, including Korea, to regenerate and replace damaged organs or tissue in the body, organ and tissue transplants are increasing. However, donors for organ transplants are increasingly scarce, and thus organ and tissue transplants are not smoothly progressing. Therefore, to solve these problems, research is being conducted to develop artificial tissue and organs. Generally, to develop artificial tissue and organs, a 3D scaffold has been manufactured using cell macro-encapsulation, electrospinning, micromolding or lithography. In addition, a method of injecting cells suitable for tissue and an organ to be formed into a 3D scaffold and providing a suitable culture environment to the injected cells, thereby finally forming artificial tissue and organs, has been used.

3D bioprinting may be used to produce a 3D construct by placing cells and a biocompatible material interacting with the cells at a specific site through stacking. Unlike conventional methods having limitations in the formation of a complicated and detailed 3D construct, 3D bioprinting is a technique that can overcome the above-mentioned limitation and has emerged as the next generation leader in artificial tissue and organ development.

To apply artificial tissue and organs formed by 3D bioprinting for actual clinical use, the size of a 3D construct has to increase. However, the larger the size of the 3D construct, the longer the formation process and the retention time of cells during the 3D bioprinter. Therefore, cell viability and functionality may be degraded, and artificial tissue and organs to be manufactured may not function smoothly. In addition, cell macro-encapsulation, which is a technique generally used to form artificial tissue and organs, has a problem of hypoxia occurring in cells encapsulated by a biocompatible hydrogel.

For this reason, to solve artificial tissue and organ issues, it is necessary to develop a 3D construct that increases the size of a structure and does not cause hypoxia in cells.

DISCLOSURE

Technical Problem

The present invention is directed to providing a 3D hydrogel scaffold which includes a first hydrogel block containing cells to be implanted in vivo and a second hydrogel block, wherein the first hydrogel block and the second hydrogel block are assembled with each other and have different biodegradabilities, and a method of producing the same.

Technical Solution

To attain the objects, one aspect of the present invention provides a 3D hydrogel scaffold, which includes a first hydrogel block containing cells to be implanted in vivo; and a second hydrogel block, wherein the first hydrogel block and the second hydrogel block are assembled with each other and have different biodegradabilities.

The term "hydrogel" used herein is a hydration gel, which is a material having a 3D hydrophilic polymer network structure formed by crosslinking water-soluble polymers using a physical bond, for example, a hydrogen bond, a Van-der-Waals force, a hydrophobic interaction, the crystallization of polymers or a chemical bond (covalent bond). A natural polymer used as a material for a hydrogel is a polymer derived from a natural material, an animal or the human body, and has very excellent biocompatibility. Therefore, a hydrogel prepared of a natural polymer may not only have less of an inflammatory response after being transplanted in vivo, but also provide excellent biofunctionality and biodegradability.

The term "hydrogel block" used herein refers to a constituent unit made of a hydrogel to assembly a 3D hydrogel scaffold, and there may be multiple hydrogel blocks having various shapes and sizes according to the design, size and shape of a 3D hydrogel scaffold to be produced.

The term "first hydrogel block" or "second hydrogel block" is used to distinguish hydrogel blocks having different properties, and the implementation of the present invention is not limited by the above terms. In addition, the term "first" or "second" may be used interchangeably according to a material for a hydrogel block and a material encapsulated in a hydrogel block.

In one embodiment of the present invention, the first hydrogel block and/or the second hydrogel block may have one or more holes, which may be formed through the first hydrogel block and/or the second hydrogel block. The hole provides a space in which the first hydrogel block or second hydrogel block is assembled with a different hydrogel block. The term "hole" used herein refers to a concave space formed by recessing a hydrogel block or an empty space formed through a hydrogel block.

In one embodiment of the present invention, the first hydrogel block may contain cells to be implanted in vivo, and serves to support the cells until they are engrafted in vivo. The first hydrogel block may consist of a polymer selected from alginate, heparin, hyaluronic acid, collagen and gelatin or a mixture thereof, and preferably, alginate.

In one embodiment of the present invention, the cells contained in the first hydrogel block may be any type corresponding to a transplantation purpose without limitation, and may be contained in the form of a cell spheroid. In addition, since the volume of the hydrogel block is significantly larger than that of the cells contained in the hydrogel block, the cells may be contained in the hydrogel block regardless of concentration.

Meanwhile, the first hydrogel block and/or the second hydrogel block may contain a growth factor. When a growth factor is simply encapsulated in a hydrogel, the growth factor is released through a pore in the hydrogel, and therefore, the release of the growth factor may be prevented by conjugating a hydrogel with the growth factor. For example, a collagen (type 1) hydrogel block having a collagen-binding domain (CBD) may be formed, and then a growth factor may be encapsulated in the first or second hydrogel block by bringing the growth factor connected with a linker that can bind to CBD into contact with the hydrogel block.

In the present invention, the growth factor may be selected from the group consisting of an epidermal growth factor (EGF), a fibroblast growth factor (FGF), a transforming growth factor β (TGFβ), a platelet-derived growth factor (PDGF), a vascular endothelial growth factor (VEGF), an insulin-like growth factor 1 (IGF-1), thioredoxin (TRX), a stem cell factor (SCF), a hepatocyte growth factor (HGF), a human growth hormone (HGH) and angiogenin, but the present invention is not limited thereto.

In one embodiment of the present invention, the second hydrogel block is assembled with the first hydrogel block to improve mechanical properties of the 3D hydrogel scaffold. The second hydrogel block may be assembled with the first hydrogel through a projection corresponding to a hole of the first hydrogel block, or due to a shape corresponding to a hole of the first hydrogel block.

In one embodiment of the present invention, the first hydrogel block and/or the second hydrogel block may have a donut or lattice shape. For example, when the first hydrogel block is a donut shape, the second hydrogel block may be assembled into an empty space in the donut shape. When the first hydrogel block is a lattice shape, the second hydrogel block may be assembled into an empty space in the lattice, and multiple second hydrogel blocks may be assembled in the first hydrogel block.

In one embodiment of the present invention, the second hydrogel block may consist of a polymer selected from the group consisting of alginate, heparin, hyaluronic acid, collagen and gelatin or a mixture thereof, and preferably, a mixture of alginate and collagen.

In one embodiment of the present invention, the first hydrogel block and the second hydrogel block may have different biodegradabilities, and the second hydrogel block may be degraded first, and then the first hydrogel block containing cells to be implanted in vivo may be degraded. For example, the structure of the first hydrogel block may be maintained for 30 days or longer such that the cells contained therein are able to be engrafted in vivo, and the second hydrogel block may be degraded within 2 to 14 days to promote angiogenesis and oxygen supply to the first hydrogel block.

Therefore, the first hydrogel and the second hydrogel may have different components and/or concentrations to control biodegradability.

In one embodiment of the present invention, the hole may be formed by recessing the first hydrogel block or passing through the first hydrogel block, and one or more holes may be formed. The hole provides a space enabling assembly of the second hydrogel block, and widens the surface area of the first hydrogel block such that oxygen can flow in the block.

In one embodiment of the present invention, when the 3D hydrogel scaffold is implanted in vivo, since the first hydrogel block and the second hydrogel block have different biodegradabilities, the second hydrogel block is first degraded, and angiogenesis and oxygen supply to the first hydrogel block is promoted, resulting in increases in the engraftment ratio and viability of implanted cells.

Another aspect of the present invention provides a method of producing a 3D hydrogel scaffold, which includes: (a) forming a first hydrogel block by printing a mixture of a biodegradable first hydrogel solution and cells by 3D bioprinting; (b) forming a second hydrogel block by printing a biodegradable second hydrogel solution by 3D bioprinting; and (c) assembling the first hydrogel block and the second hydrogel block.

The term "3D bioprinting" used herein is one of the techniques of 3D printing, which is technology of producing a 3D construct by placing cells and a biocompatible material interacting therewith at a specific site by stacking. Currently, for skin, organ or bone transplantation, a donated tissue or organ is mostly used, but it is difficult to find a suitable tissue or organ for transplantation, and although having been transplanted, there is a problem relating to an autoimmune response. To overcome such a problem, research has been conducted to produce various artificial substitutes such as artificial bones, blood vessels, skin and organs using a polymer material having biodegradability and biocompatibility.

In one embodiment of the present invention, the method of producing a 3D hydrogel scaffold may further include curing the hydrogel blocks printed after Steps (a) and (b). The curing step may be performed by immersing the printed hydrogel block in a solution containing a bivalent cation such as a magnesium ion ($Mg^{2+}$) or a calcium ion ($Ca^{2+}$), for example, a calcium chloride solution.

In one embodiment of the present invention, the first hydrogel solution and the second hydrogel solution may be solutions in which one or more polymers selected from alginate, heparin, hyaluronic acid, collagen and gelatin are dissolved, and includes a mixed solution of polymers.

In one embodiment of the present invention, the first hydrogel solution and the second hydrogel solution preferably have different components. For example, as the first hydrogel solution, an alginate solution (0.5 to 5% (w/w)) may be used, and as the second hydrogel solution, a mixed solution in which an alginate solution (0.5 to 5% (w/w)) and a collagen solution (0.5 to 5 mg/mL) are mixed at 1:1 (v/v) may be used.

In one embodiment of the present invention, the first hydrogel block and/or the second hydrogel block may have one or more holes, which may be formed through the first hydrogel block and/or the second hydrogel block.

In one embodiment of the present invention, in the step of printing the first hydrogel block and the second hydrogel block by 3D bioprinting, specific printing conditions may vary according to the designs, components or concentrations of the first and second hydrogel blocks. The variable printing conditions include a printing speed, an input flow, a filling density, and the size of a syringe nozzle from which a hydrogel solution is printed. For example, the first and second hydrogel blocks may be printed under conditions of a printing speed of 5 to 20 mm/s, an input flow of 50 to 100% and a filling density of 50 to 100%.

Advantageous Effects

Since a 3D hydrogel scaffold of the present invention can become larger through the assembly of blocks, and have excellent viability of implanted cells and different biodegradabilities of the blocks, a risk of hypoxia for cells is reduced.

DESCRIPTION OF DRAWINGS

In FIG. 19, the word "DAPI" stands for 4',6-diamidino-2-phenylindole.

[Modes of the Invention]

Hereinafter, the present invention will be described in further detail with reference to examples. These examples are merely provided to illustrate the present invention, and it should not be not construed that the scope of the present invention is not limited by the following examples.

Example 1: Formation of Parts of 3D Printer for Producing 3D Construct

A holder that can fix a disposable 1 mL syringe to a 3D bioprinter was designed by AutoCAD. After heat treatment, a poly lactic acid (PLA) filament was extruded at a high temperature and cooled at room temperature, thereby finally forming a syringe holder formed of PLA.

A printing bed was designed to fix 35 Φ, 60 Φ and 100 Φ culture dishes to a 3D bioprinter, and then customized according to the specifications. The formed syringe holder and the printing bed for fixing a culture dish (hereinafter, referred to as a printing bed) were attached to the 3D bioprinter, and then a random 3D construct was produced. As a result, it was confirmed that the syringe holder and the printing bed operated normally.

FIG. 1 shows (a) the structures of parts of a syringe holder, (b) the syringe holder with which a disposable syringe is assembled, (c) the design of a printing bed for fixing a culture dish, (d) a formed printing bed, and (e) an image of the use of the printing bed.

Example 2: Preparation of Gelatin Slush and Production of 3D Construct Using the Same 2-1. Preparation of Gelatin Slush Solution I was prepared by adding 10 mM calcium chloride and 10 mM 2-[4-(2-hydroxyethyl)piperazin-1-yl] ethanesulfonic acid (HEPES) to deionized water. A gelatin solution was prepared by dissolving gelatin (gelatin type A from procine skin) in the solution I at a concentration of 4.5% (w/v), and storing in a freezer for 24 hours to solidify. 150 mL of the solution I was added to the solidified gelatin solution, and grinded with a blender (BL311E, Tefal) for 30 seconds at a two-level speed. The ground gelatin solution was centrifuged for 3 minutes at 4000 rpm and 4° C. to remove the solution I (upper layer). The solution I was added to a gelatin slush formed in a pellet, and the gelatin slush was suspended again using a vortexer. To remove bubbles from the gelatin slush, a sonicator was set to MAX, and then the gelatin slush was sonicated for 3 minutes at 25° C. The above-described process was repeated four times, and then the gelatin slush was stored at 4° C. Afterward, the frequency of a rheometer was set to 1 to 100 Hz to determine the viscoelasticity of the gelatin slush prepared as described above.

Figure 1A:
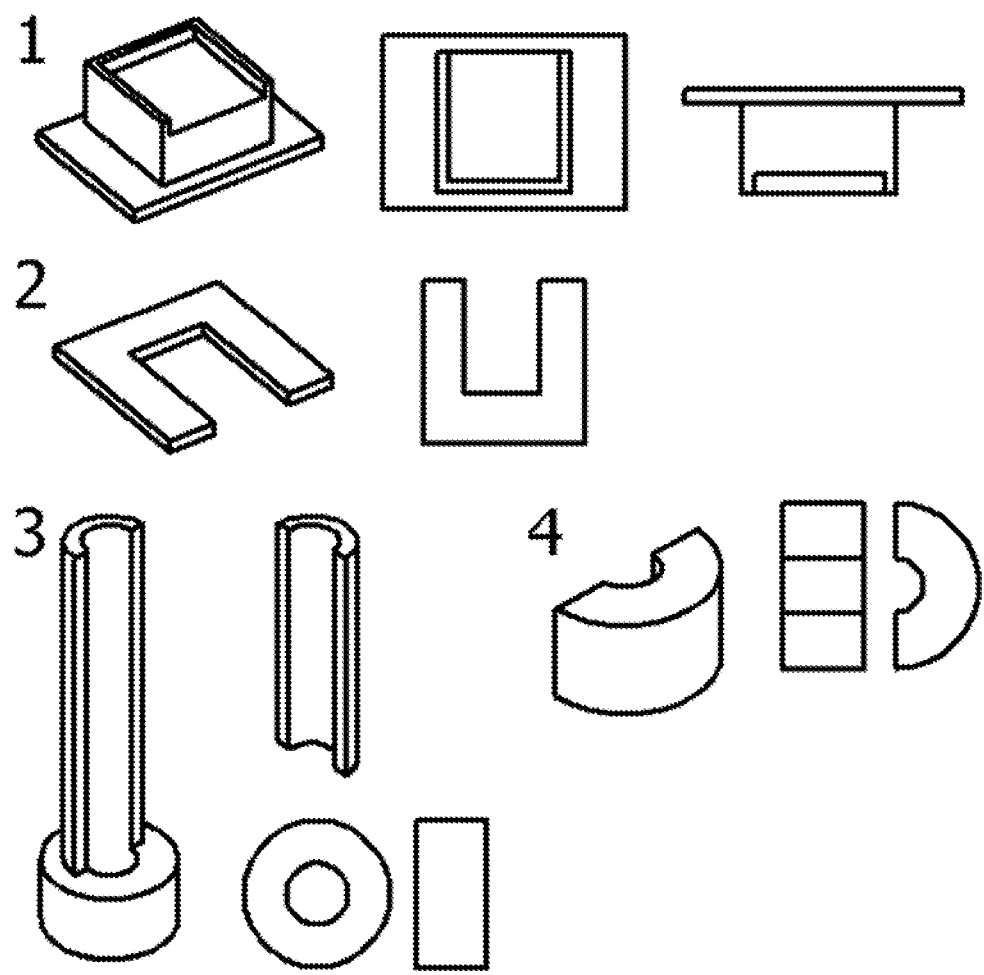
FIG. 1 shows (a) the structures of parts of a syringe holder, (b) the syringe holder with which a disposable syringe is assembled, (c) the design of a printing bed for fixing a culture dish, (d) a formed printing bed, and (e) an image of the use of the printing bed.
Figure 1B:
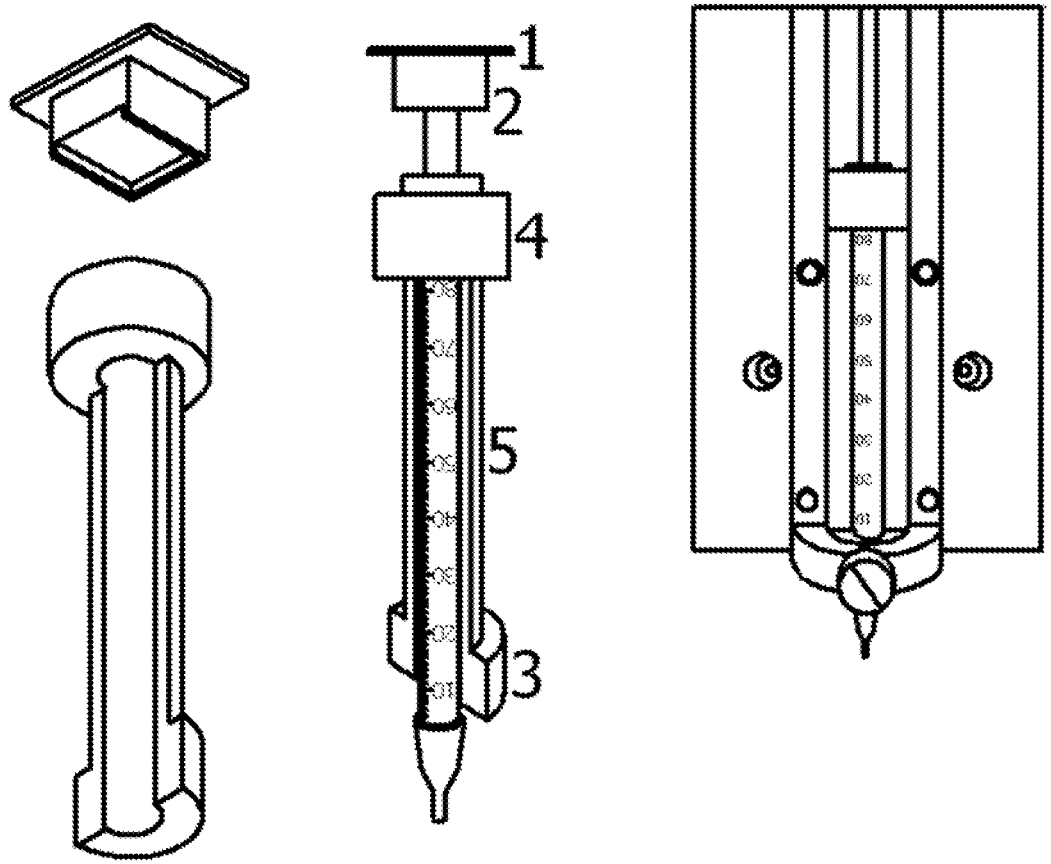
Figure 1C:
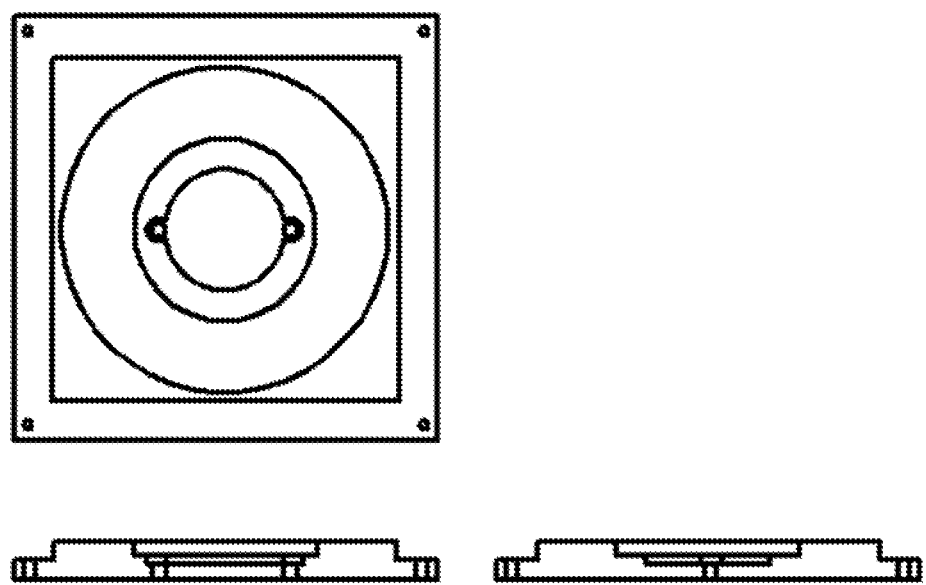
Figure 1D:
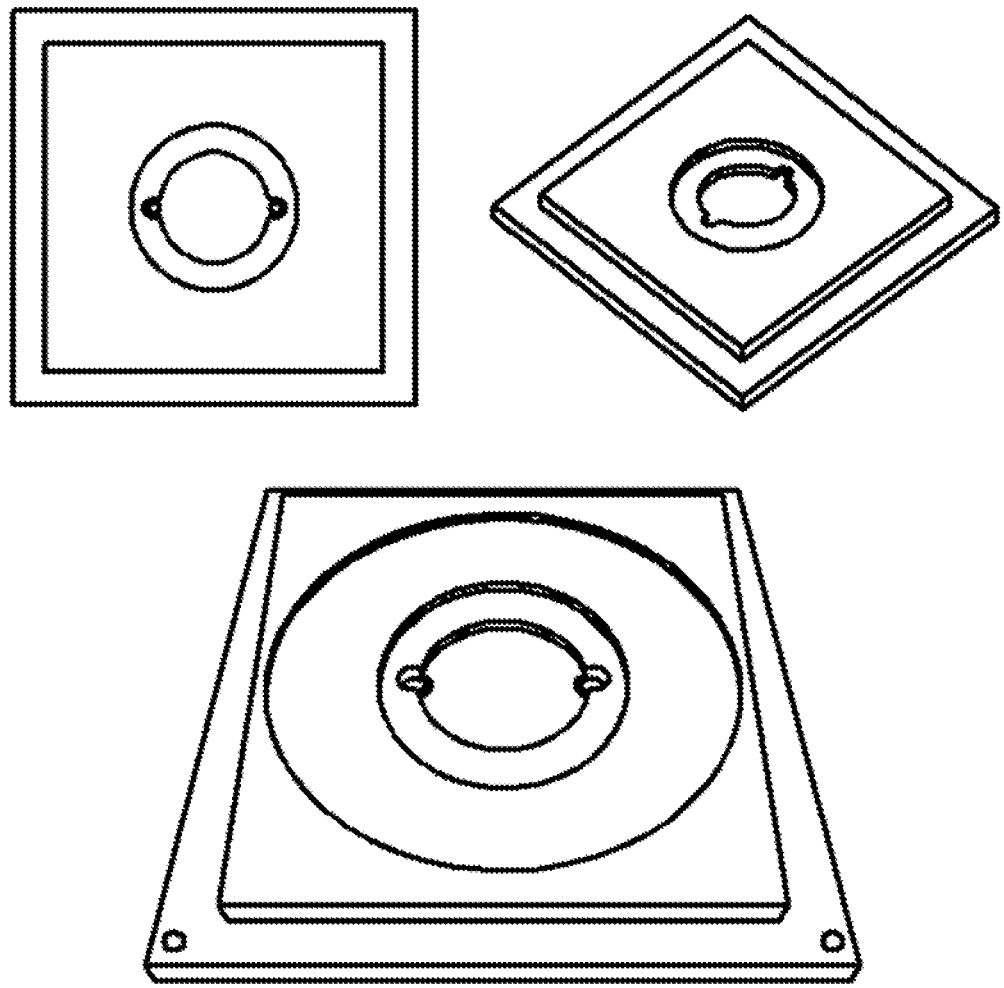
Figure 1E:
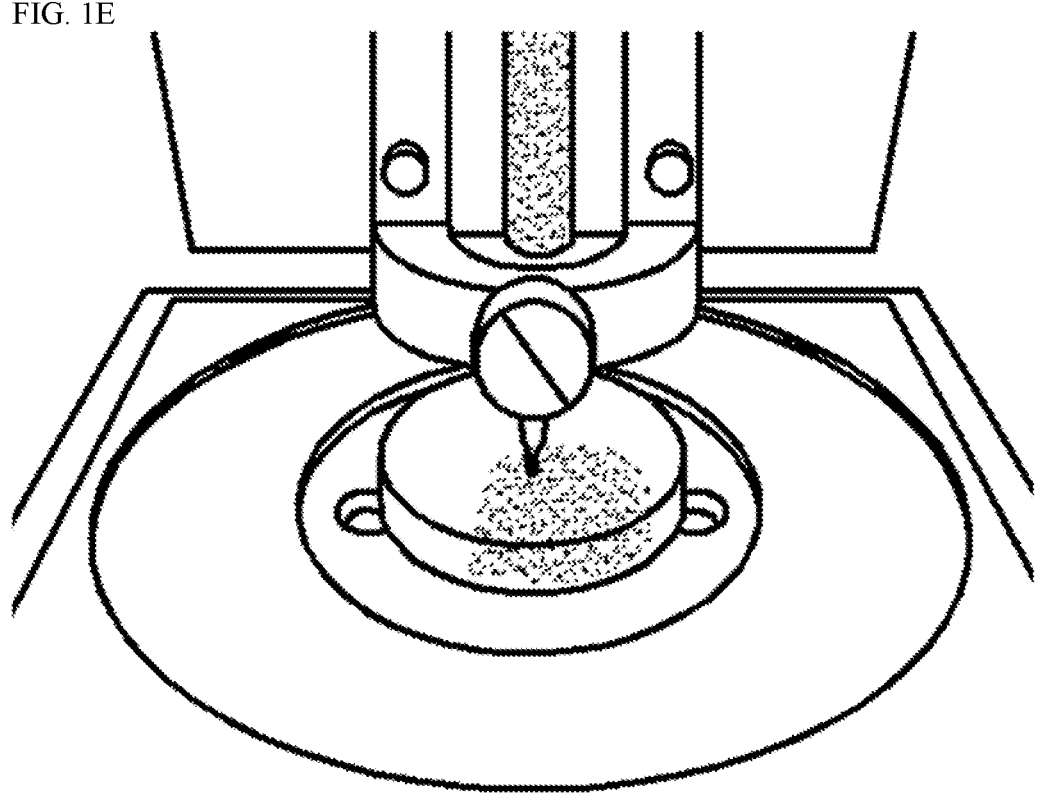
Figure 2:
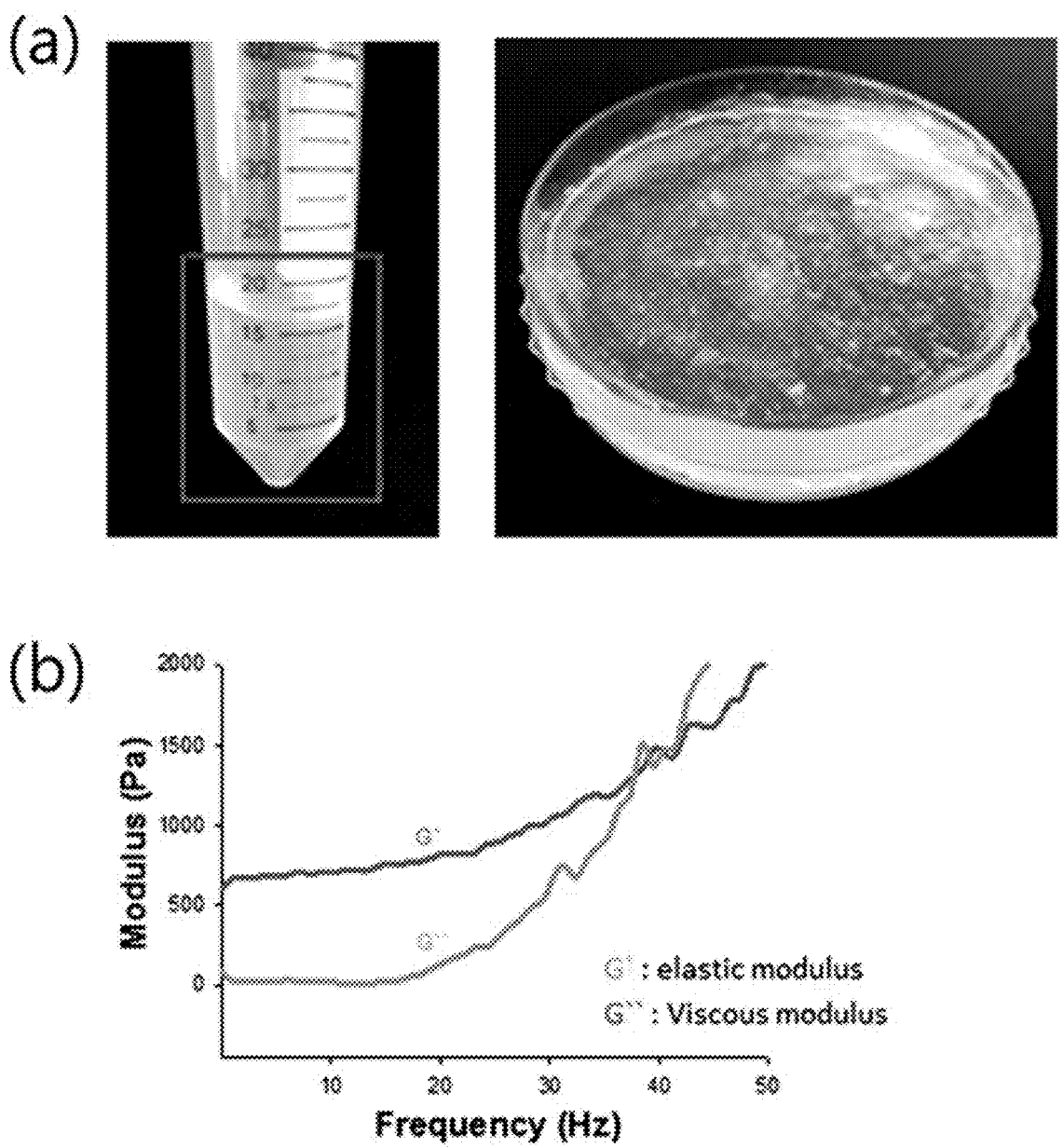
FIG. 2 shows (a) a prepared gelatin slush and (b) the result of confirming the viscoelasticity thereof using a rheometer.

As a result, as shown in FIG. 2(b), since an elastic modulus was higher than a viscous modulus at a specific frequency or less, the gelatin slush is known to exhibit the behavior of a solid. However, the reversal between the elastic modulus and the viscous modulus occurred at a specific frequency or more, thereby showing the behavior of a liquid, and the viscoelasticity of the gelatin slush was confirmed.

2-2. Printing of 3D Construct Using Gelatin Slush

To confirm the properties of the gelatin slush prepared in Example 2-1, a 3D construct was printed by the following method.

Solution II was prepared by dissolving 0.9% (w/w) sodium chloride and 2% (w/w) alginate in deionized water. To impart fluidity, the gelatin slush was stored in a 37° C. constant-temperature bath for 2 minutes and transferred to a culture dish flatly, and then the culture dish was fixed to the printing bed. The solution II was filled in a 1 mL disposable syringe and a syringe for 3D printing, the syringes were fixed to a syringe holder, and then a syringe fixing part was fixed in a 3D printer. When the solution II was discharged into the culture dish containing the gelatin slush, an alginate hydrogel was formed by reacting alginate contained in the solution II with a calcium ion ($Ca^{2+}$) in the gelatin slush. The culture dish was incubated for 20 minutes at 37° C. to liquidize the gelatin slush, and a 3D construct of the alginate hydrogel in the gelatin slush was collected. To improve the strength of the 3D construct, the 3D construct was immersed in a solution containing 100 mM calcium chloride and 10 mM HEPES for 3 minutes. Finally, the 3D construct was washed with HEPES buffer to remove calcium ions around the construct.

The shape of the produced alginate hydrogel 3D construct was confirmed with the naked eye. In addition, it was confirmed that the 3D construct has stability with sufficient strength by stretching in different directions.

Figure 3:
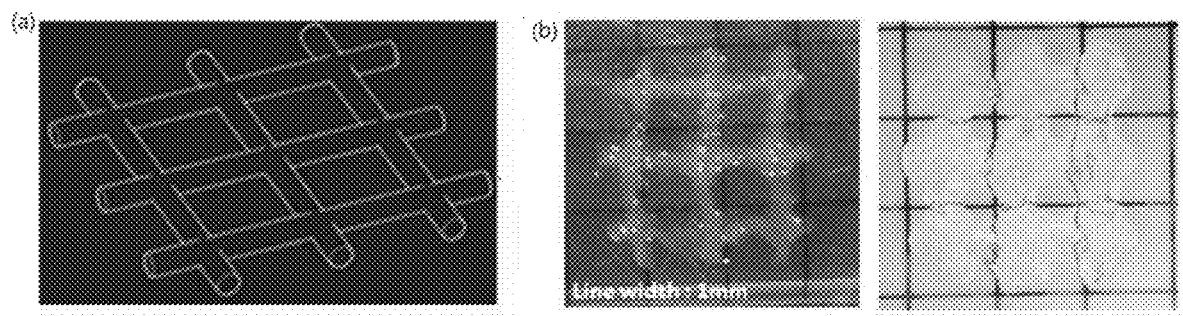
FIG. 3 shows (a) the design of a lattice-shaped 3D construct and (b) an alginate hydrogel prepared according to the design.

FIG. 3 shows (a) the design of a lattice-shaped 3D construct and (b) an alginate hydrogel prepared according to the design.

Example 3: Optimization of 3D Bioprinting Settings 3-1. Printing Speed Optimization 3D constructs having the same design were printed by the same method as described in Example 2-2, except that the printing speed of a 3D bioprinter was set to 10, 12, 14 and 16 mm/s, respectively. The specifications of the printed 3D constructs were comparatively analyzed using an image analysis program.

Figure 4A:
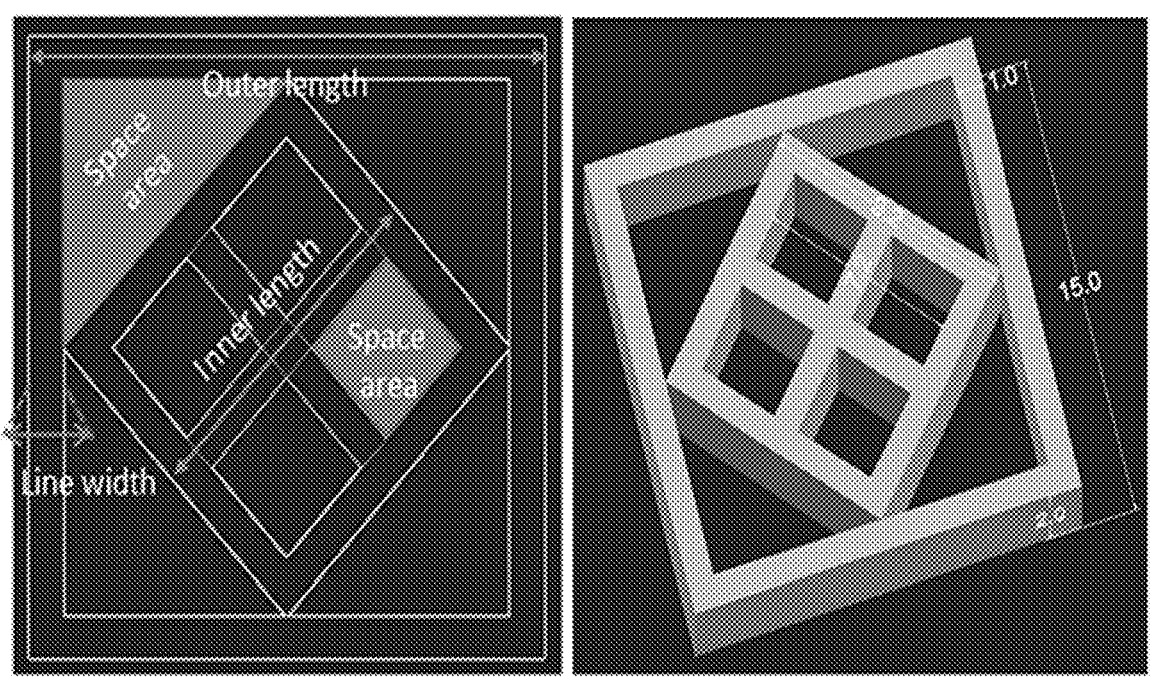
FIG. 4A shows a 3D construct designed by AutoCAD.
Figure 4B:
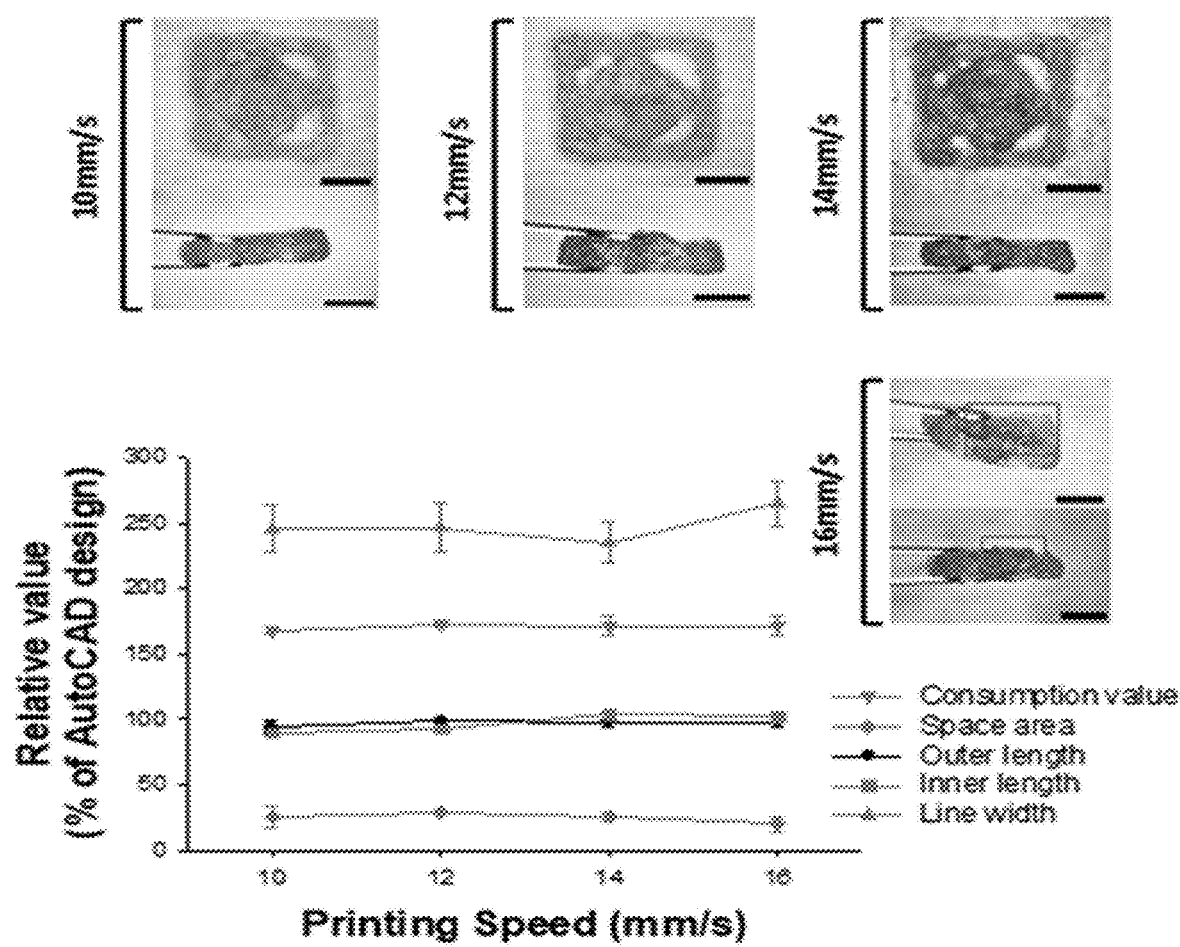
FIG. 4B shows the results of confirming the shape and relative specifications of a 3D construct according to a printing speed.
Figure 4C:
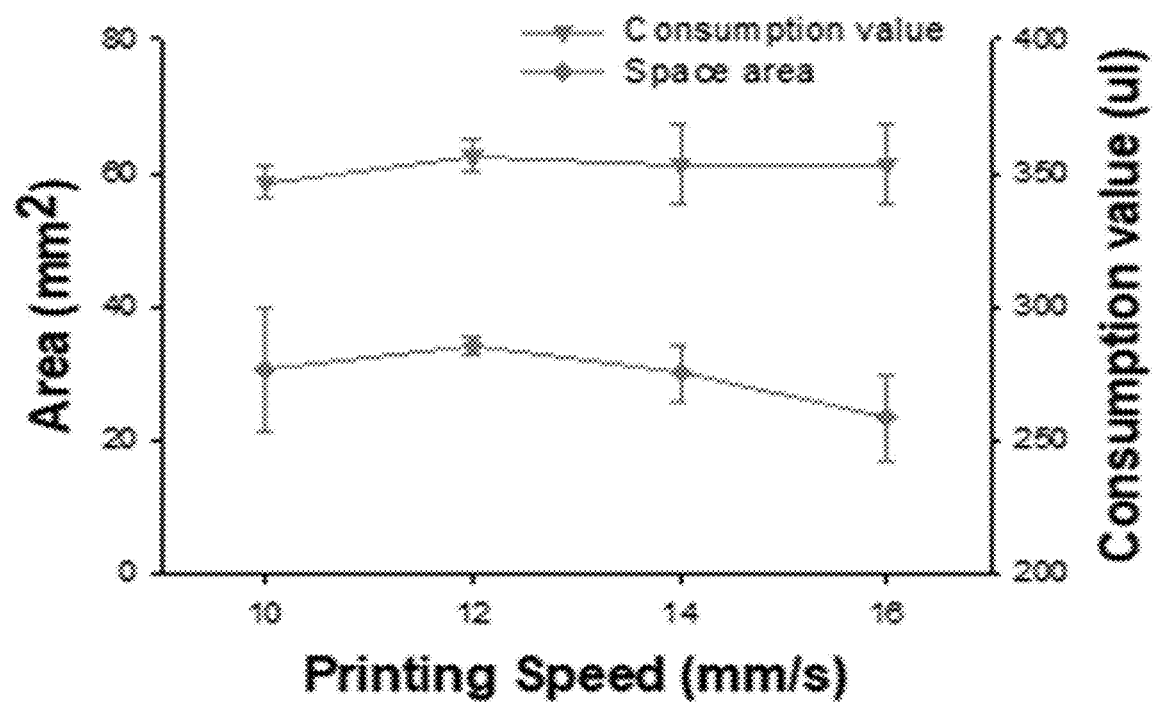
FIG. 4C shows the results of measuring absolute specifications of a 3D construct according to a printing speed.
Figure 4C:
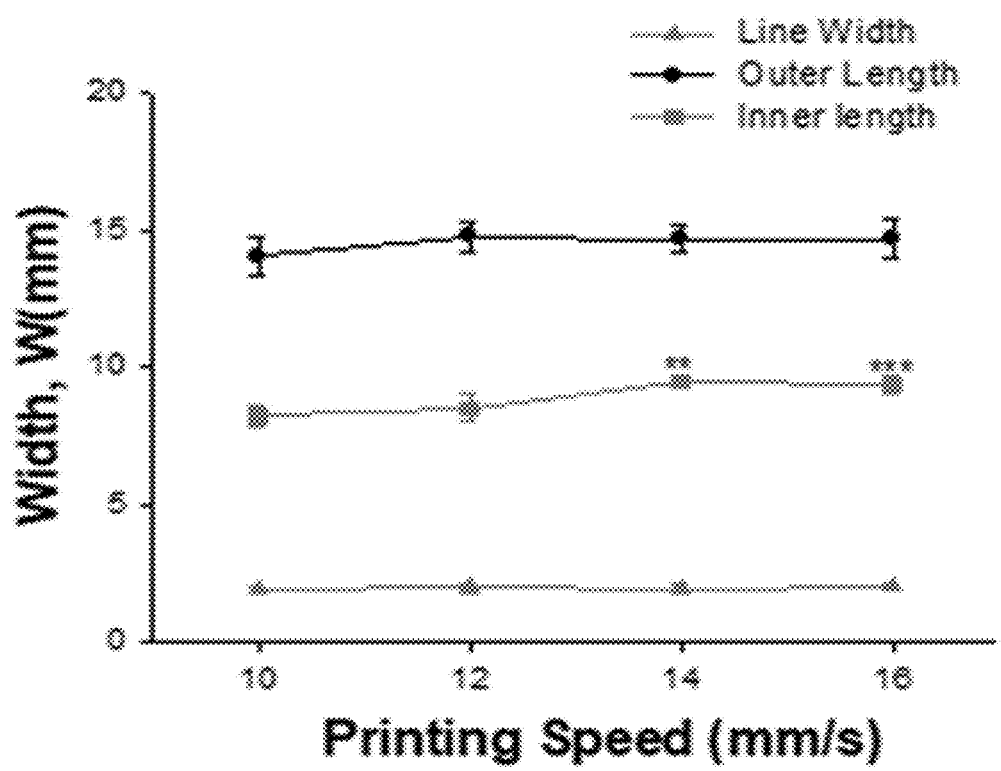

As a result, as shown in FIGS. 4B and 4C, when the printing speed was 12 mm/s, it was confirmed that the 3D construct was produced with the most similar specifications to the drawing designed by AutoCAD. In addition, when the printing speed was 16 mm/s, since the height of the produced construct was irregular, the printing speed was determined to be 12 mm/s at which the printing time was approximately 8 minutes. Afterward, the 3D construct was produced at a printing speed of 12 mm/s.

TABLE 1

| Printing speed (mm/s) | Printing time (s) |
|---|---|
| 10 | 9:09 |
| 12 | 8:07 |
| 14 | 7:29 |
| 16 | 6:53 |

3-2. Input Flow Optimization

A 3D construct was produced with specifications similar to those designed by AutoCAD, and to confirm whether a hydrogel precursor solution was used at an amount similar to the volume of the designed construct, an experiment of optimizing an input flow was carried out. The input flow is a setting value that determines the extrusion amount of the hydrogel precursor solution from a syringe.

In the setting values in the 3D bioprinting, the input flow was set to 100, 90, 80, 70, 65 or 60%, and 3D constructs having the same design were printed by the same method as described in Example 3-1. The specifications of the printed 3D construct were comparatively analyzed using an image analysis program.

Figure 5A:
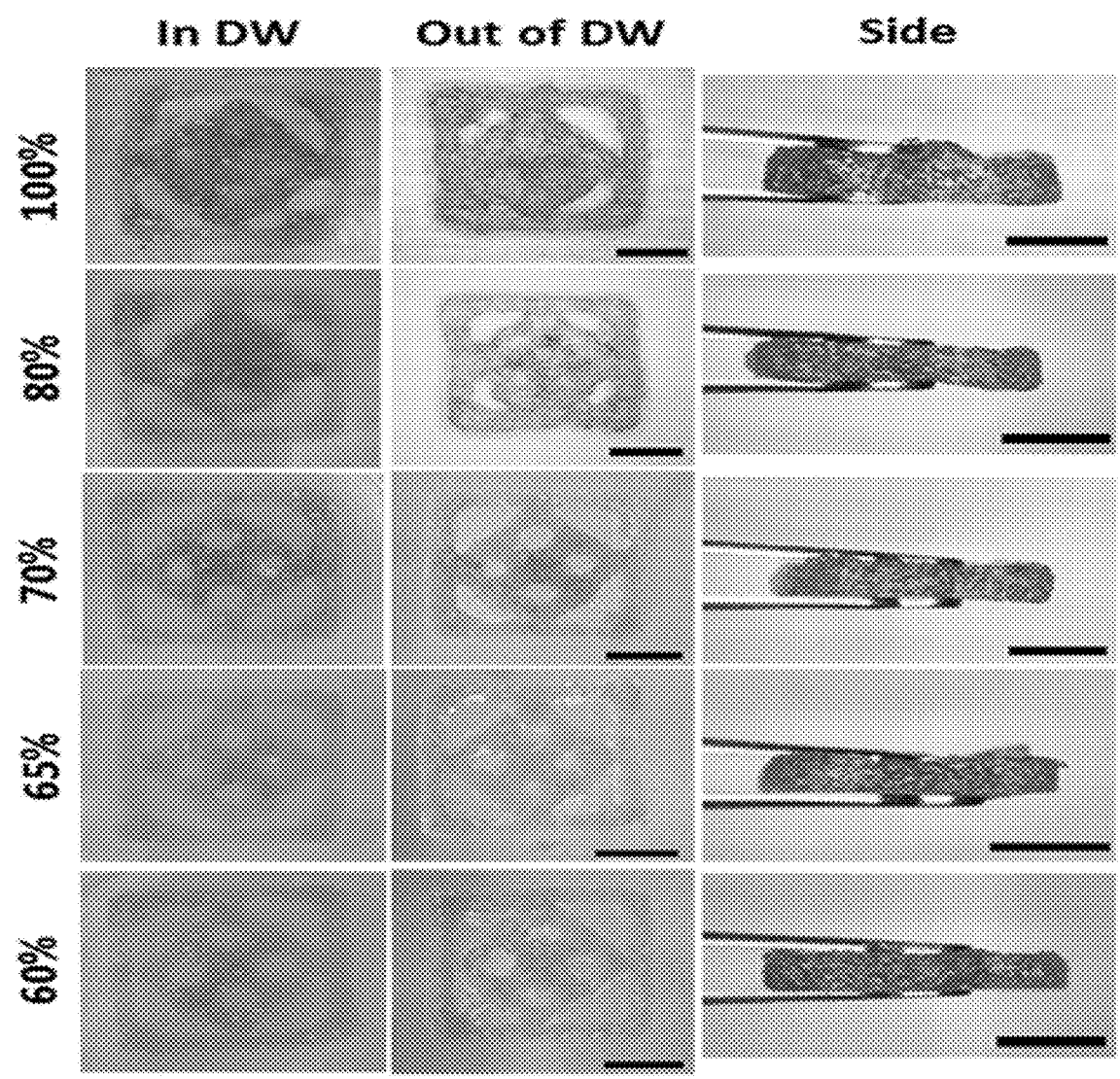
FIG. 5A shows the shapes of 3D constructs printed with different input flows.
Figure 5B:
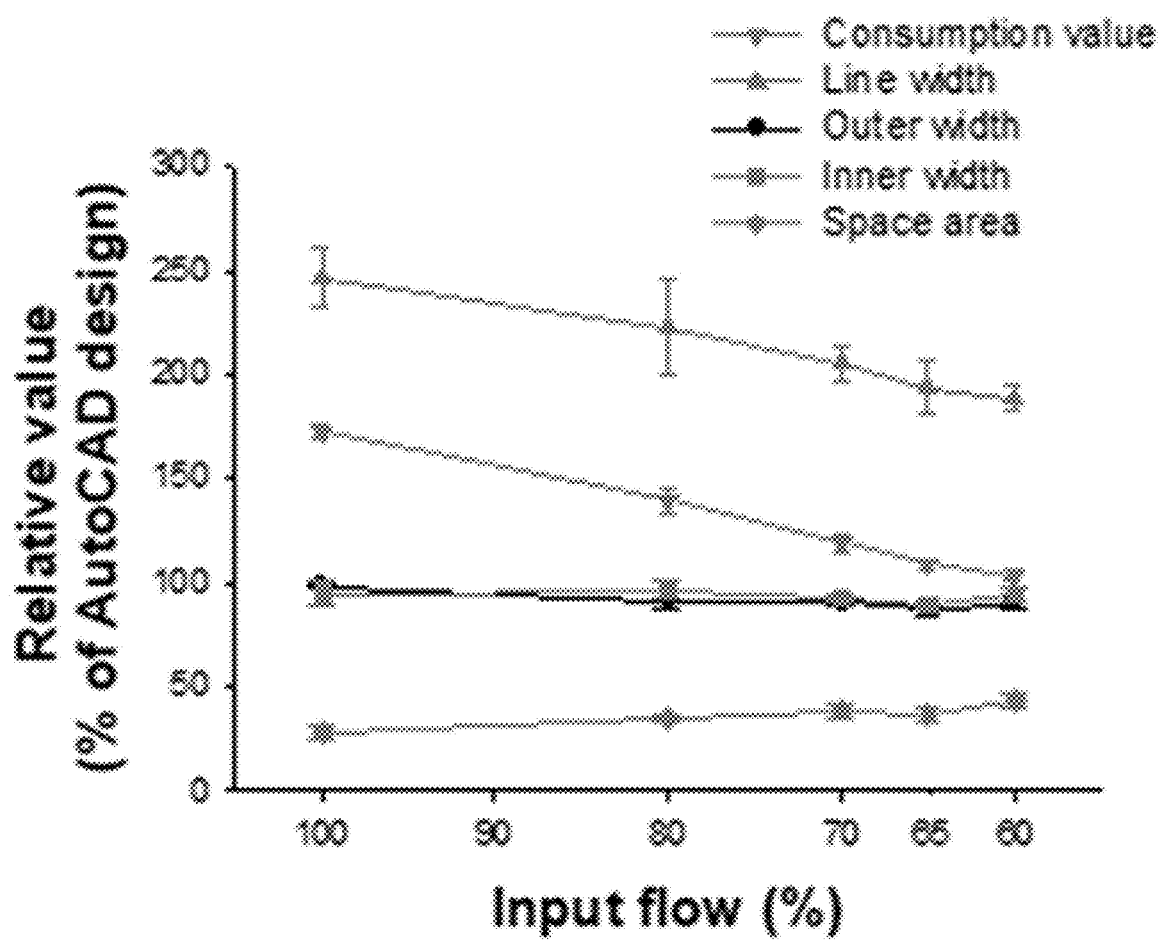
FIG. 5B shows the results of measuring relative specifications of the constructs printed with different input flows.
Figure 5C:
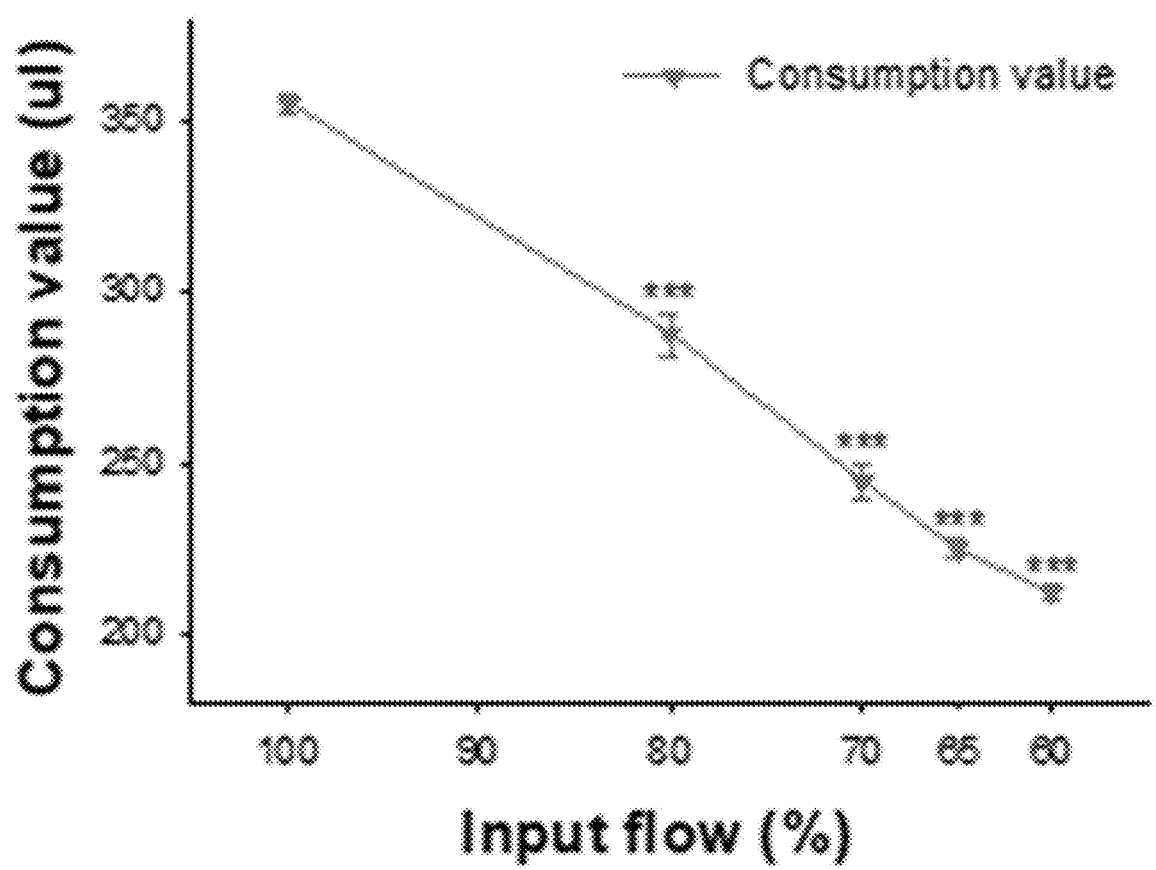
FIG. 5C shows the results of measuring absolute specifications of the constructs printed with different input flows.
Figure 5D:
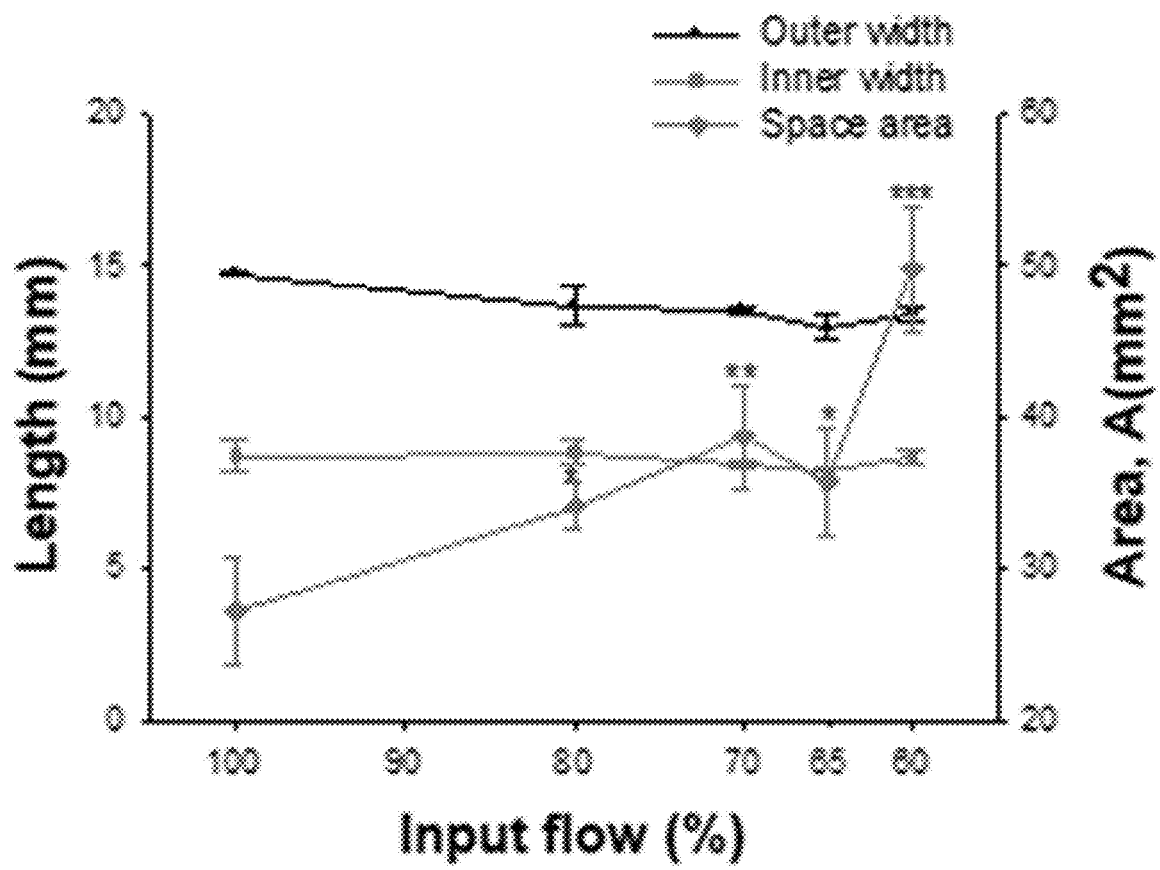
FIG. 5D shows the results of measuring lengths of the constructs printed with different input flows.
Figure 6:
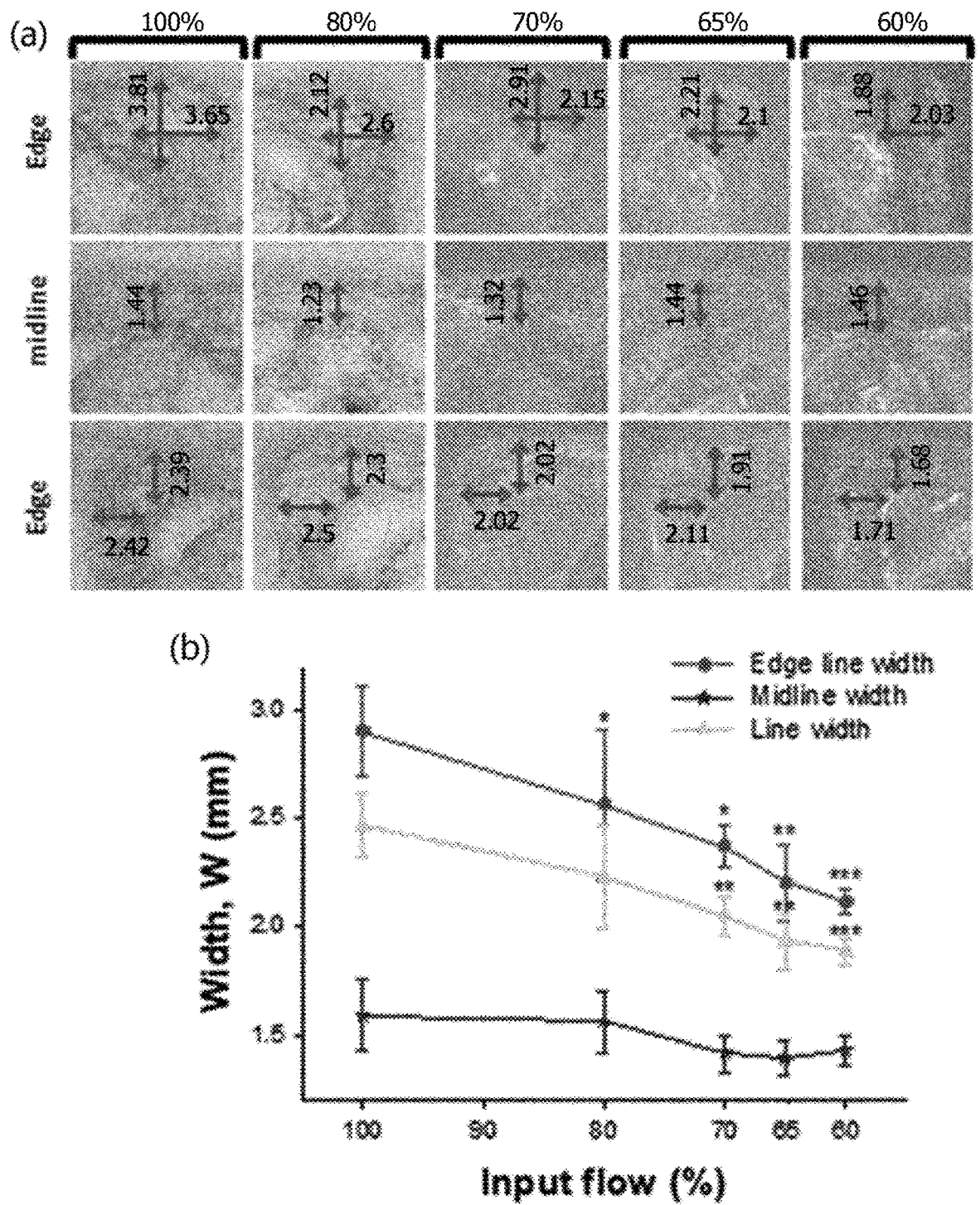
FIG. 6 shows the results of measuring (a) edge shapes and (b) edge specifications of the 3D constructs printed with different input flows.

As a result, as shown in FIGS. 5B to 5D, when the input flow was 60%, the consumption amount of a hydrogel precursor solution was almost similar to the volume of the 3D construct designed by AutoCAD. In addition, as shown in FIG. 6, since the specifications of the edge region of the printed 3D construct were most similar to those of the drawing designed by AutoCAD, compared with other input flows, the input flow was determined to be 60%. Afterward, at 3D construct was produced with an input flow of 60%.

3-3. Filling Density Optimization 3D bioprinting is a method of producing a 3D construct by drawing lines by moving a nozzle in a printer, and stacking the drawn lines. A filling density is a value setting an empty space between lines, and the height of a prepared 3D construct was able to be changed by controlling an empty space between lines according to a filling density.

In the setting values of the 3D bioprinting, as the filling density was set to 100, 90, 80 or 70%, 3D constructs having the same design were printed, and the height of the printed 3D construct was comparatively analyzed using an image analysis program.

Figure 7A:
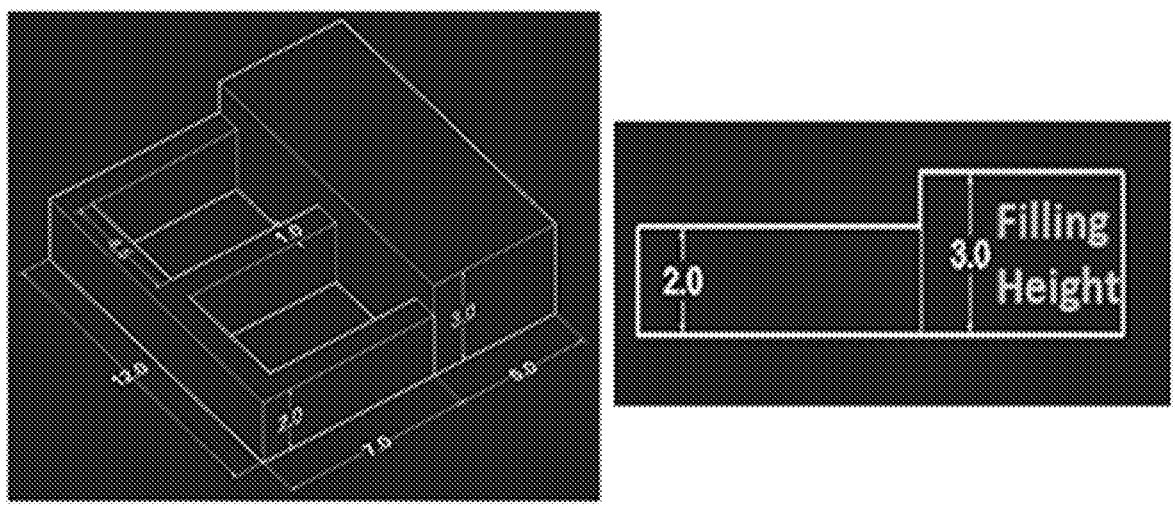
FIG. 7A shows a 3D construct designed by AutoCAD.
Figure 7B:
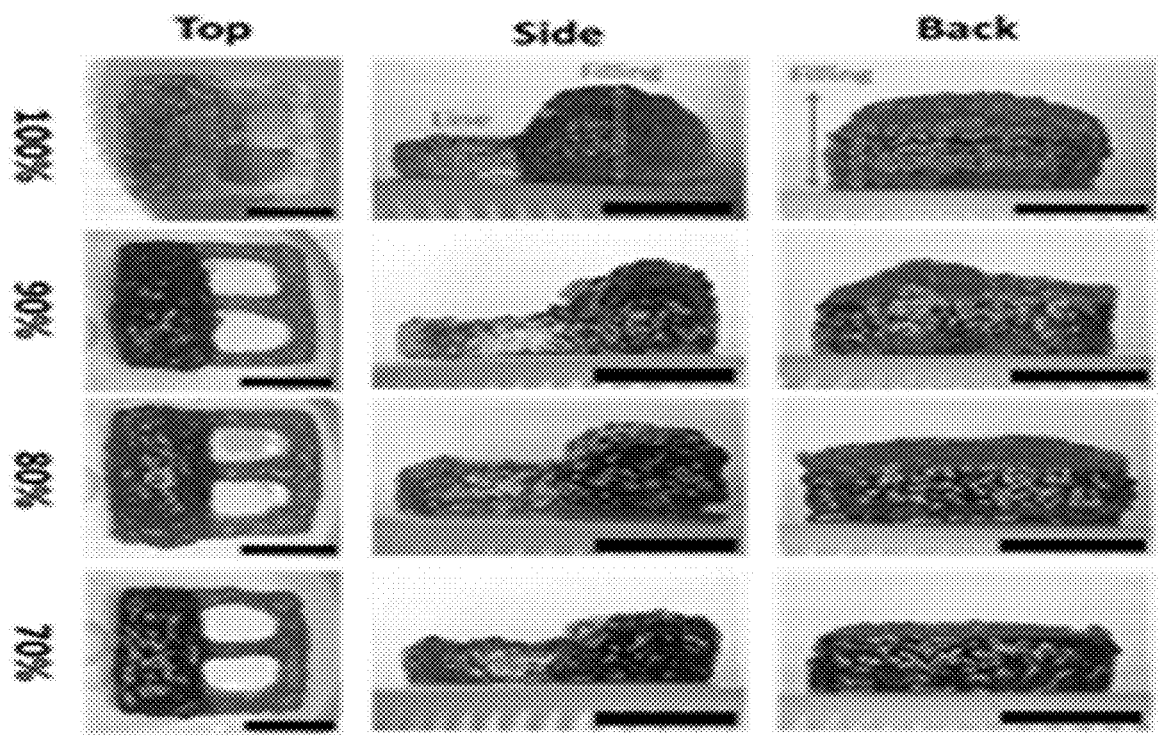
FIG. 7B shows the shapes of 3D constructs printed with different filling densities.
Figure 7C:
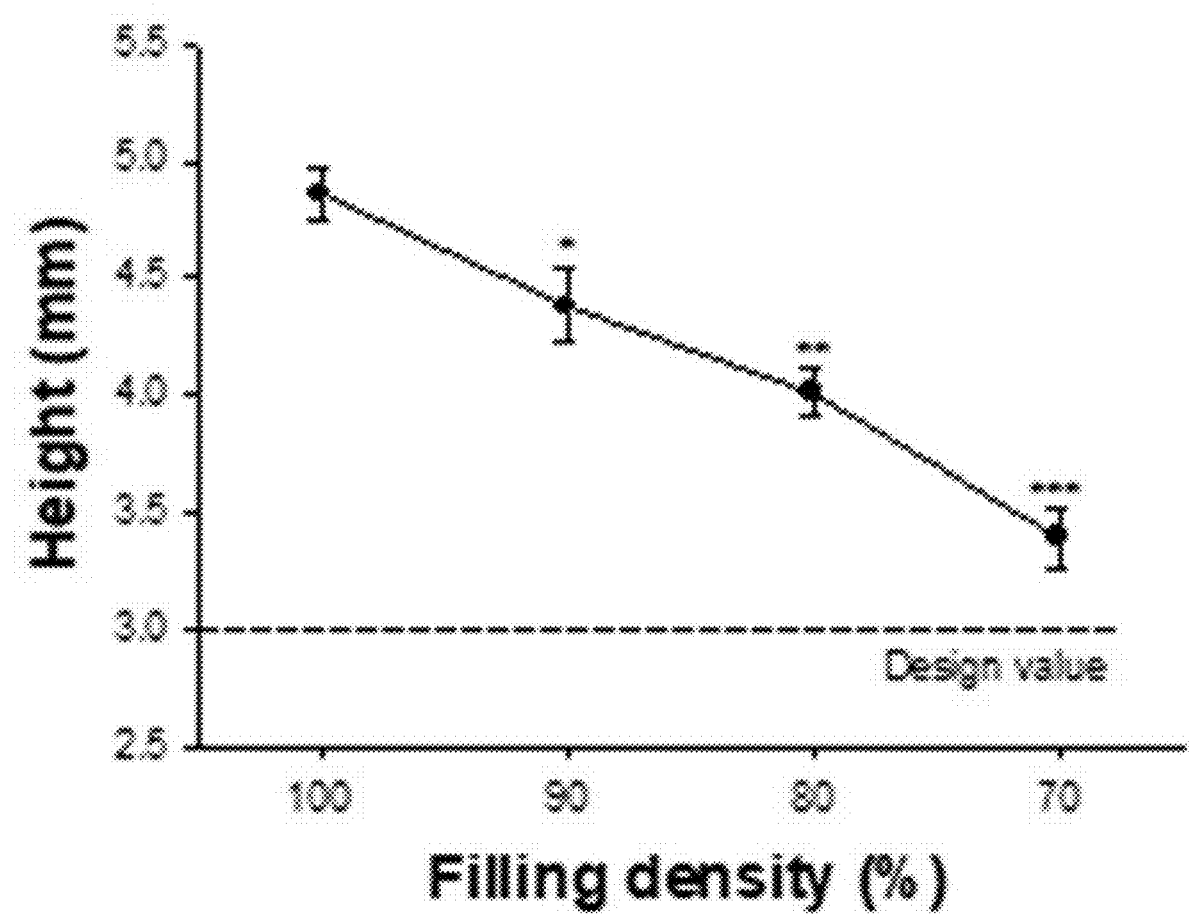
FIG. 7C shows the results of measuring absolute specifications of the printed constructs.

As a result, as shown in FIGS. 7B and 7C, when the filling density was 70%, the height of the 3D construct was approximately 3.2 mm similar to 3 mm, which is the value designed by AutoCAD. Accordingly, a subsequent 3D construct was produced with a filling density of 70%.

Example 4: Production of Assembled Construct Using Optimized Conditions and Property Evaluation 4-1. Production of Assembled Construct and Stability Evaluation A macrostructure was produced by designing various shapes of blocks by AutoCAD, printing the blocks under conditions optimized in Example 3, and assembling the printed blocks to fit these shapes. Hereinafter, the macrostructure produced by the assembling method is referred to as an assembled construct. To confirm the stability of the assembled construct, the macrostructure was put in deionized water, a rotation speed was set to 100, 200 and 300 rpm for vibration.

As a result, as shown in FIGS. 8(c) and 9(c), it was seen that, regardless of rpm, the assembled construct was not divided into blocks, and a stable assembled construct was able to be formed only by a method of assembling blocks.

Figure 8:
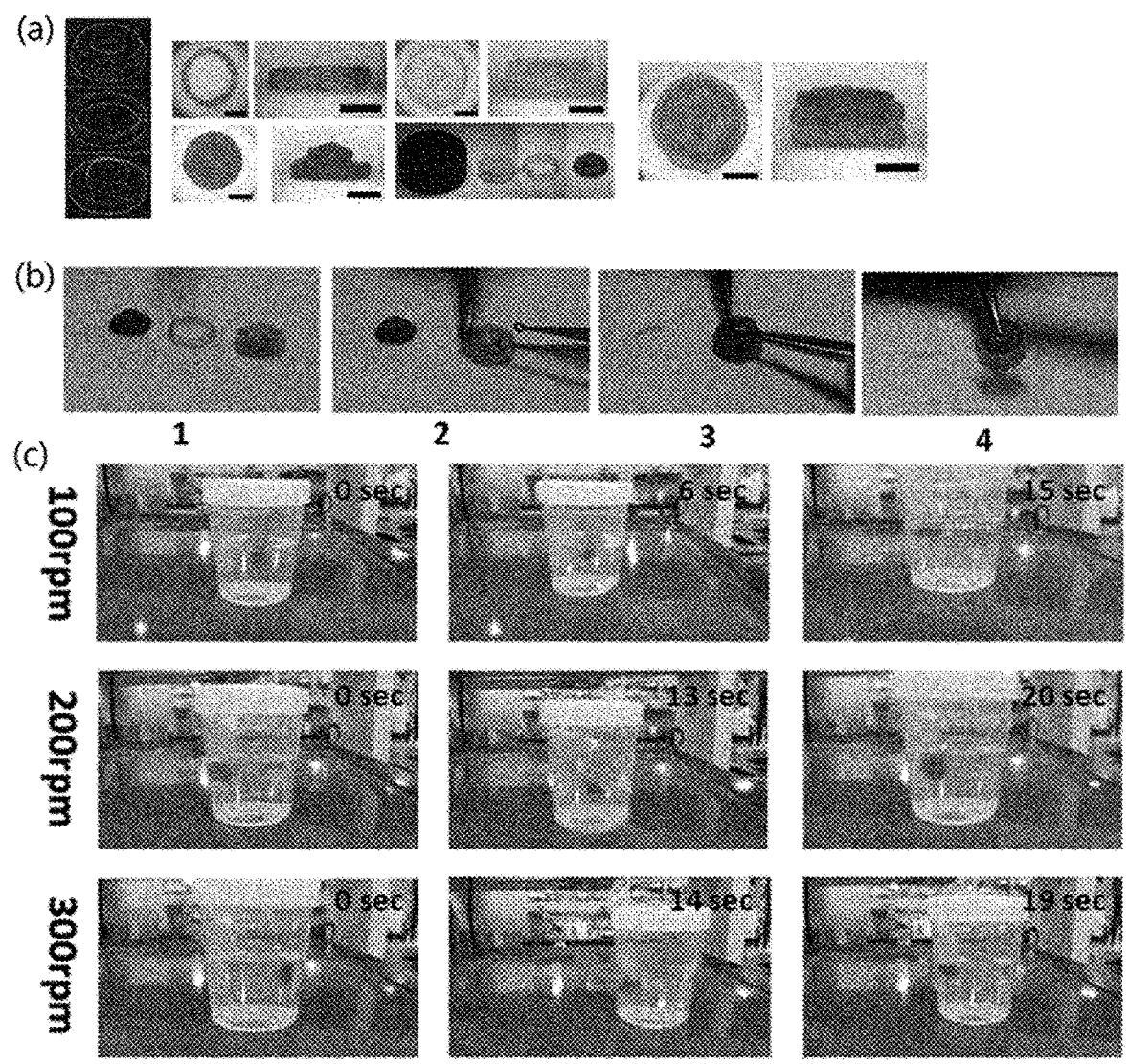
FIG. 8 shows (a) three types of blocks formed in different shapes, (b) a process of producing an assembled construct with the blocks, and (c) results of vibrating the assembled construct at different rotation speeds (rpm).

FIG. 8 shows (a) three different shapes of blocks, (b) a process of producing an assembled construct with the blocks, and (c) results of vibrating the assembled construct at different rotation speeds (rpm).

Figure 9:
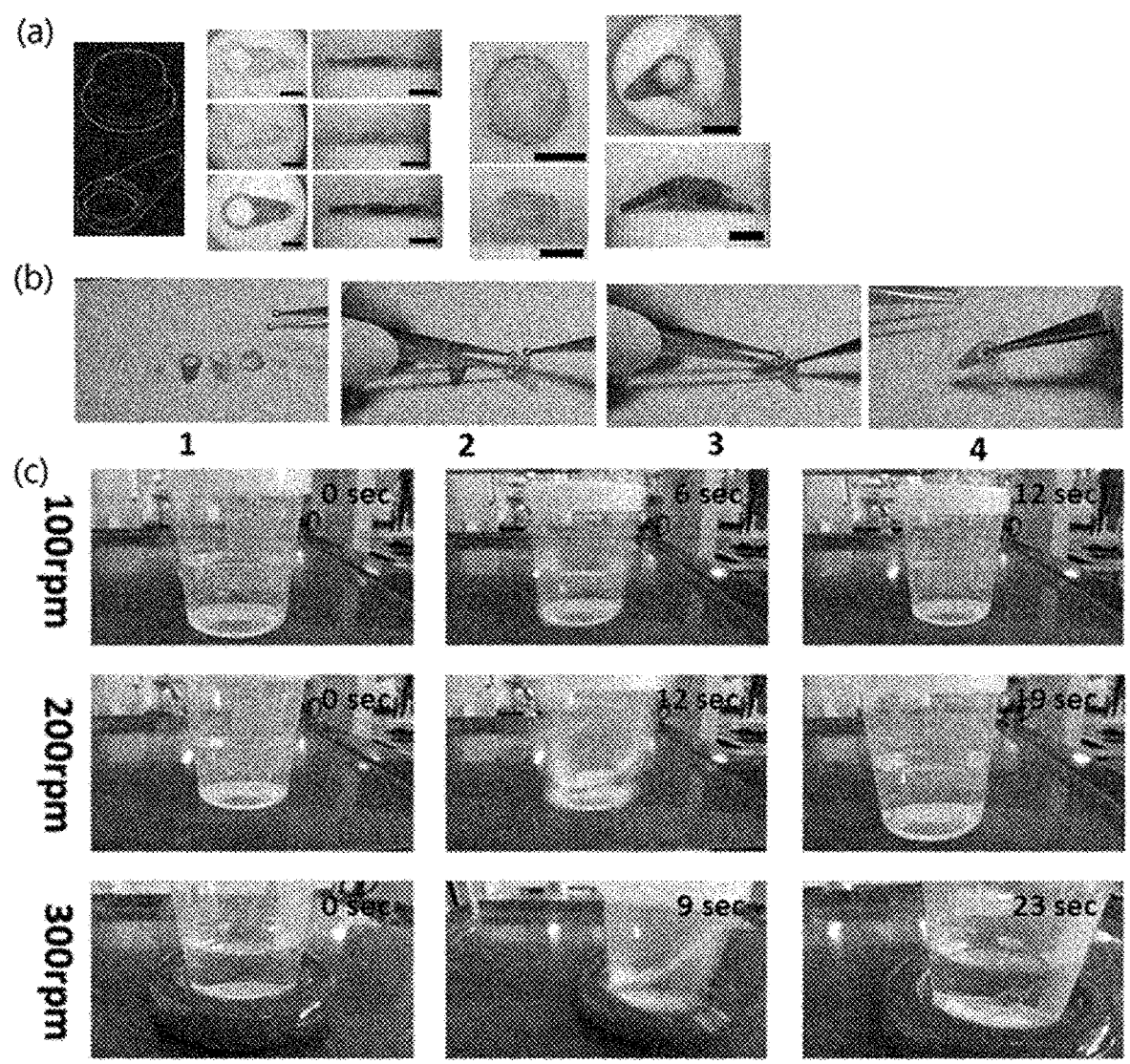
FIG. 9 shows (a) four types of blocks formed in different shapes, (b) a process of producing an assembled construct with the blocks, and (c) results of vibrating the assembled construct at different rotation speeds (rpm).

FIG. 9 shows (a) four different shapes of blocks, (b) a process of preparing an assembled construct with the blocks, and (c) results of vibrating the assembled construct at different rotation speeds (rpm).

4-2. Measurement of Mechanical Properties

Mechanical properties of the macrostructure (assembled construct) produced by a block assembling method and a macrostructure (unassembled construct) not produced by an assembling method were compared. Single blocks were referred to as block A and block B, respectively, and the assembled construct and the unassembled construct were produced with the same specifications.

Each of the blocks and macrostructures were designed by AutoCAD and then printed. Here, to make the degradabilities of the constructs different, the components of the blocks made a difference. The unassembled construct and the block A were printed with a 2.6% (w/w) alginate solution, and in the assembled construct, the block A and the block B were printed with a 2.6% (w/w) alginate solution and then assembled. The block B was printed with a solution in which a 2.6% (w/w) alginate solution and a collagen (collagen type 1 from rat tail) solution (3.6 mg/mL) were mixed at a volume ratio of 1:1.

The constructs were broken by applying a strain of 1 to 500% to each construct printed on a parallel plate of a rheometer, and then the strain and elastic/viscous moduli when the construct was broken were measured. In addition, the elastic/viscous moduli were measured by applying a frequency of 1 Hz to each construct for 60 seconds.

Figure 10A:
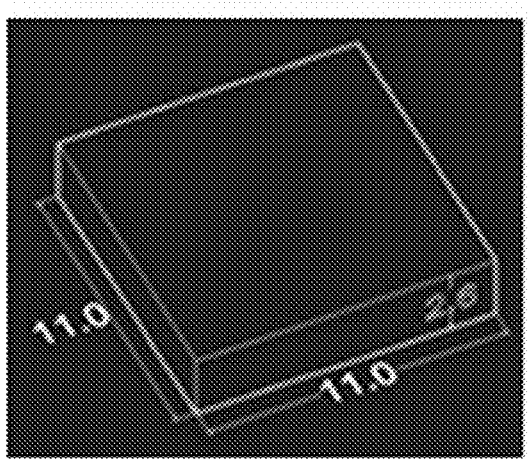
FIG. 10A shows the shape of a 3D construct designed to measure mechanical properties.
Figure 10A:
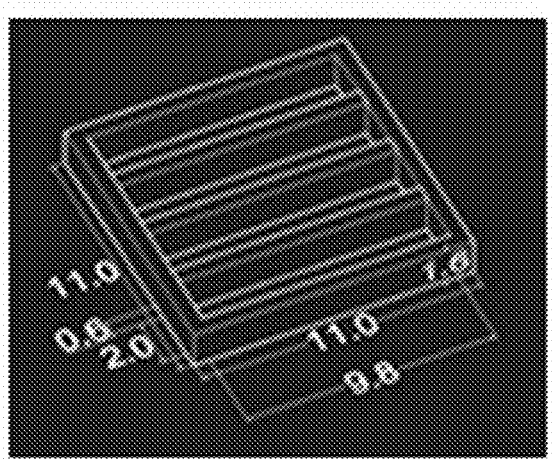
Figure 10A:
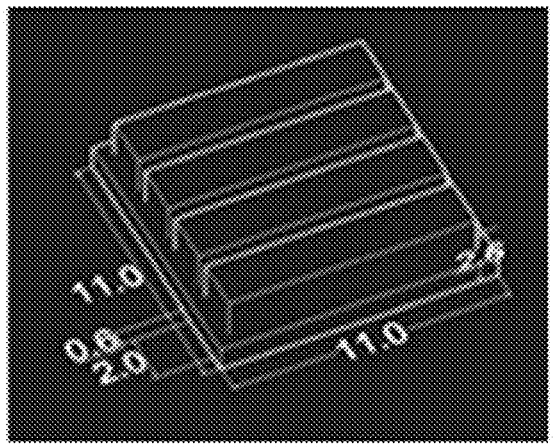
Figure 10A:
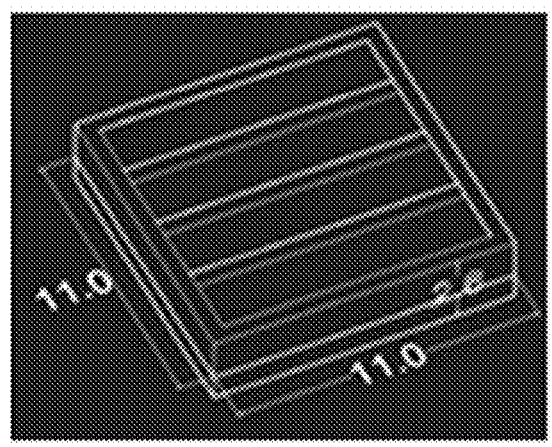
Figure 10B:
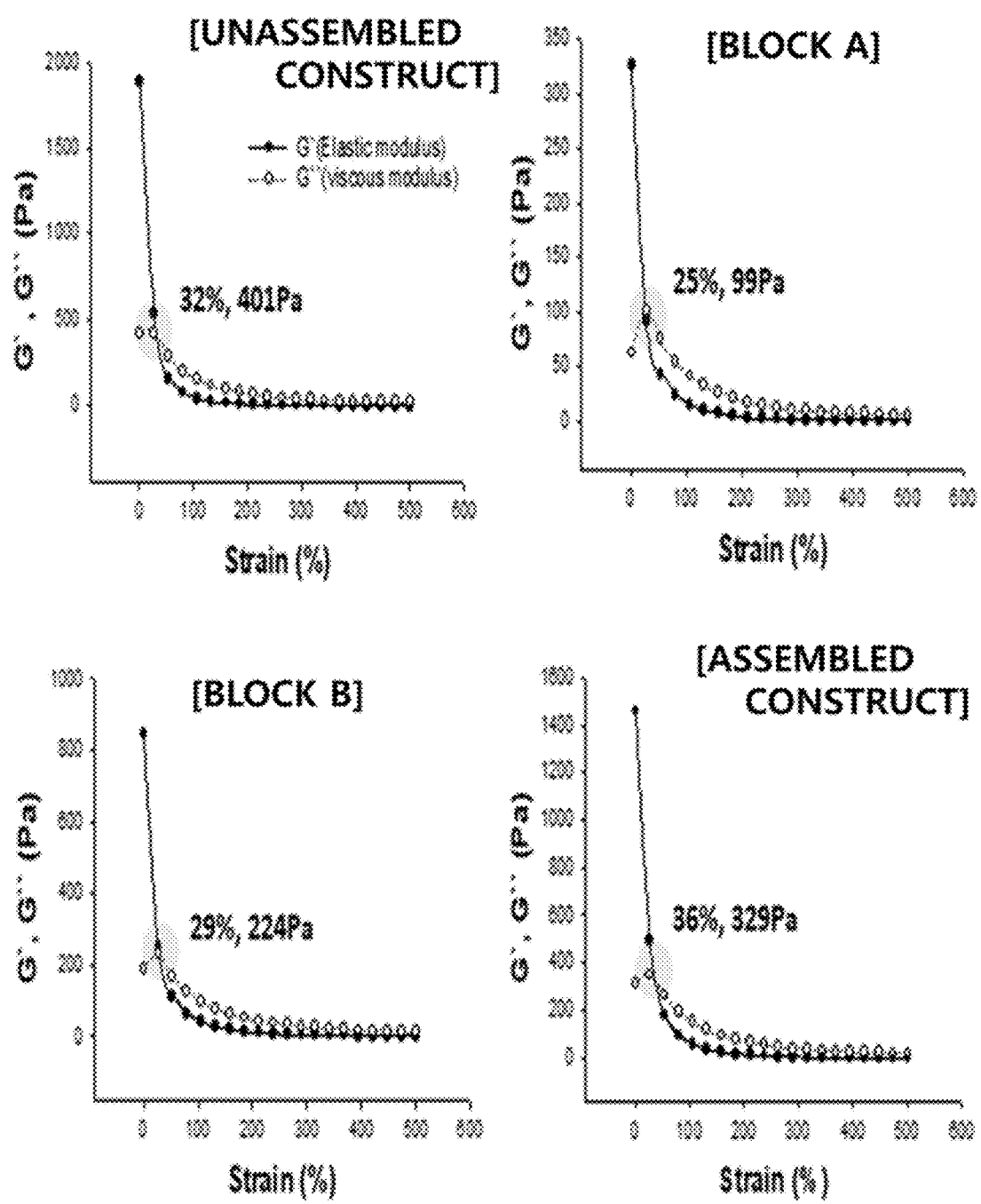
FIG. 10B shows the results of measuring elastic/viscous moduli by applying a strain to the designed construct.

As a result, as shown in FIG. 10B, it was confirmed that the strains and elastic/viscous moduli applied to the block A and the block B are lower than those of the assembled construct, and it can be seen that the assembled construct and the unassembled construct have similar strains and elastic/viscous moduli. This means that, when the blocks are assembled into one construct, mechanical properties are improved.

Figure 10C:
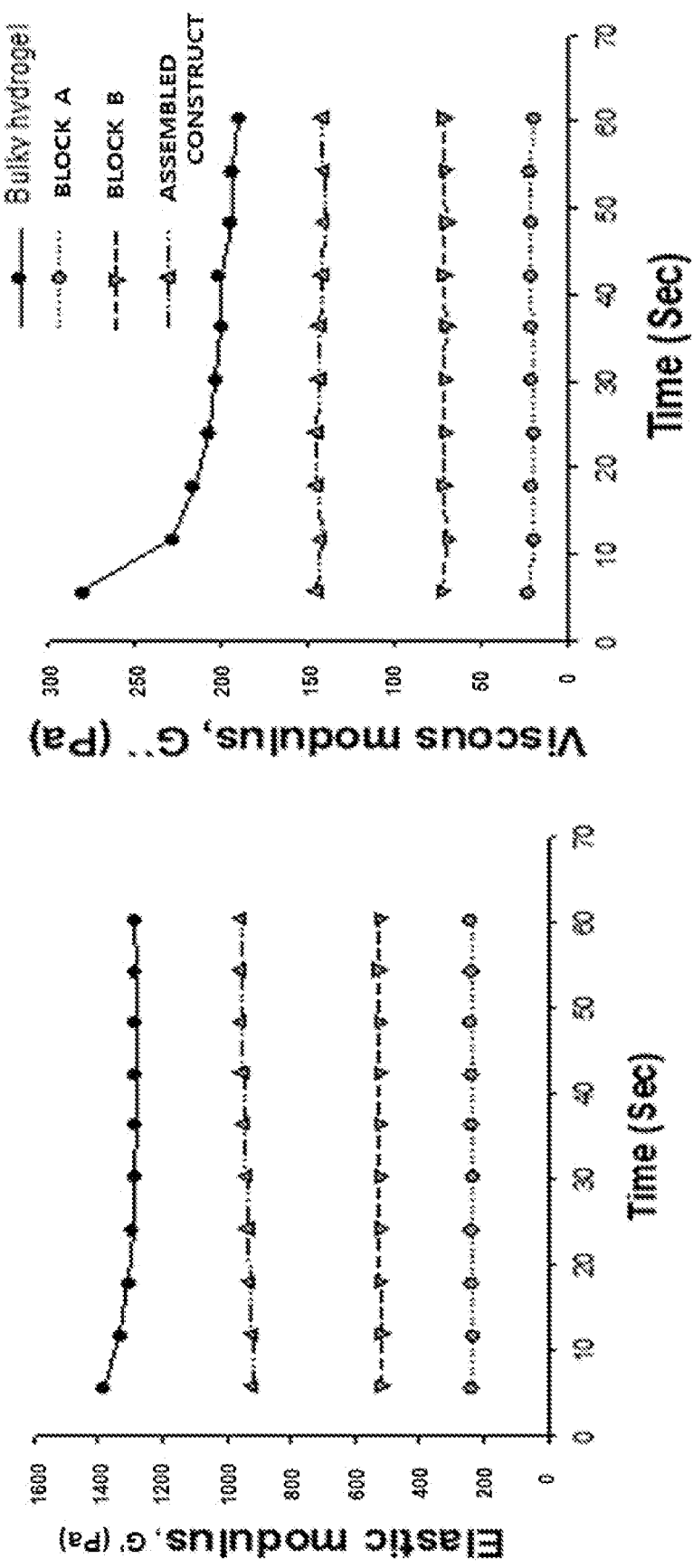
FIG. 10C shows the results of measuring elastic/viscous moduli of each construct according to time.

In addition, as shown in FIG. 10C, as a result of measuring the elastic/viscous moduli of each construct over time, the elastic/viscous moduli of the block A are approximately 200 Pa and 30 Pa, respectively, but the elastic/viscous moduli of the assembled macrostructure in which the block A and the block B are assembled are approximately 1000 Pa and 150 Pa, respectively, indicating that mechanical properties are improved. It shows that a macrostructure improved in physical properties can be produced by assembling blocks.

Example 5: Characterization of Assembled Construct Composed with Different Components and Concentrations Block B composed with different components and concentrations was formed, and assembled with the block A, thereby producing an assembled construct, and then a behavioral change of the assembled construct according to the properties of blocks was confirmed.

An unassembled construct was set as a control, and block B was formed by mixing alginate with collagen. Specifically, three types of mixed solutions in which 1 mg/mL collagen and 1, 0.75 and 0.5% (w/w) alginate were mixed were prepared by mixing a collagen solution (2 mg/mL) and an alginate solution (2, 1.5 and 1% (w/w)) in a volume ratio of 1:1, respectively. Three types of mixed solutions in which 2 mg/mL collagen and 1, 0.75 and 0.5% (w/w) of alginate were mixed were further prepared by the same method, respectively. The block B was formed with a total of 6 mixed solutions, and both the block A and the unassembled macrostructure were produced with a 2% (w/w) alginate solution. The assembled construct was produced by assembling one block A and two block Bs. Each of the prepared constructs was stored in a medium and observed for 30 days or more, and an RPMI-1640 medium (Invitrogen, USA) was replaced every 2 days.

Figure 11A:
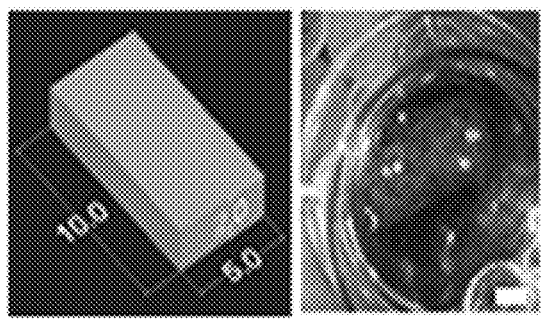
FIG. 11A shows the shape of a 3D construct produced with different components.
Figure 11A:
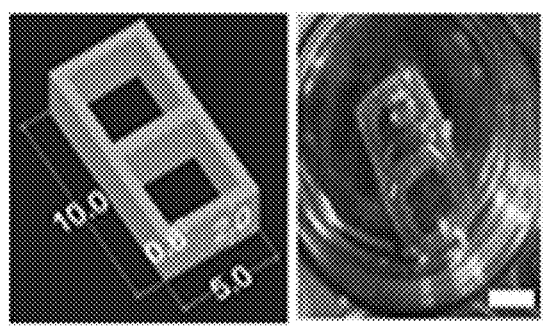
Figure 11A:
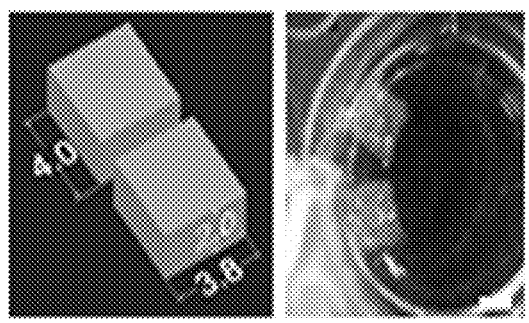
Figure 11A:
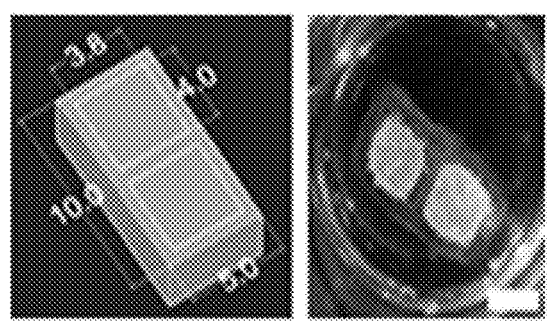
Figure 11B:
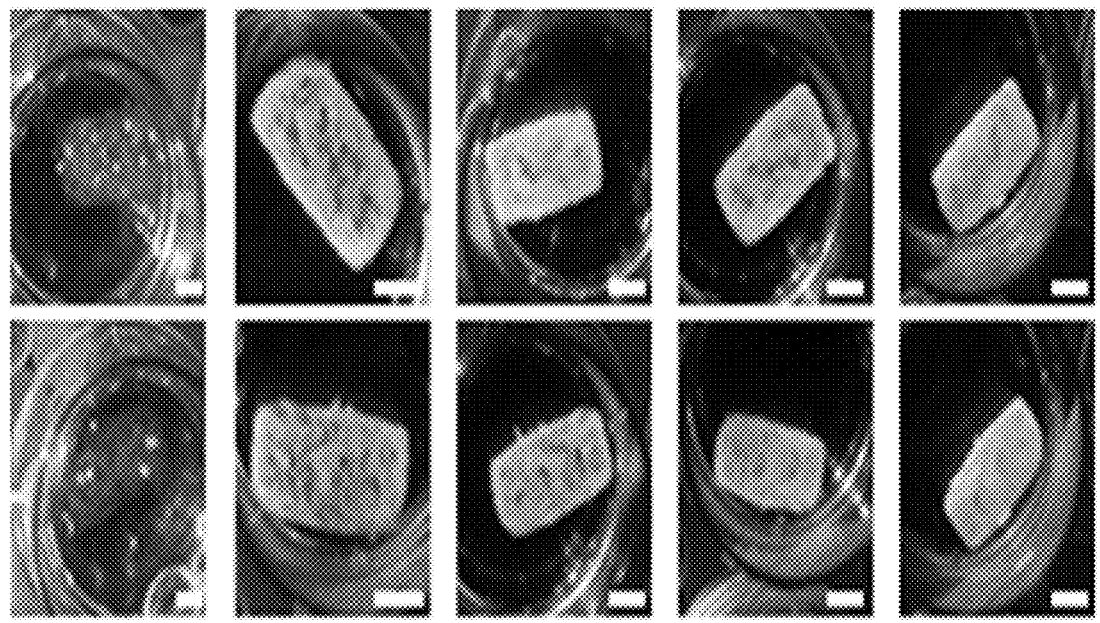
FIG. 11B shows the collapsed form of an unassembled construct and block A over time.
Figure 11B:
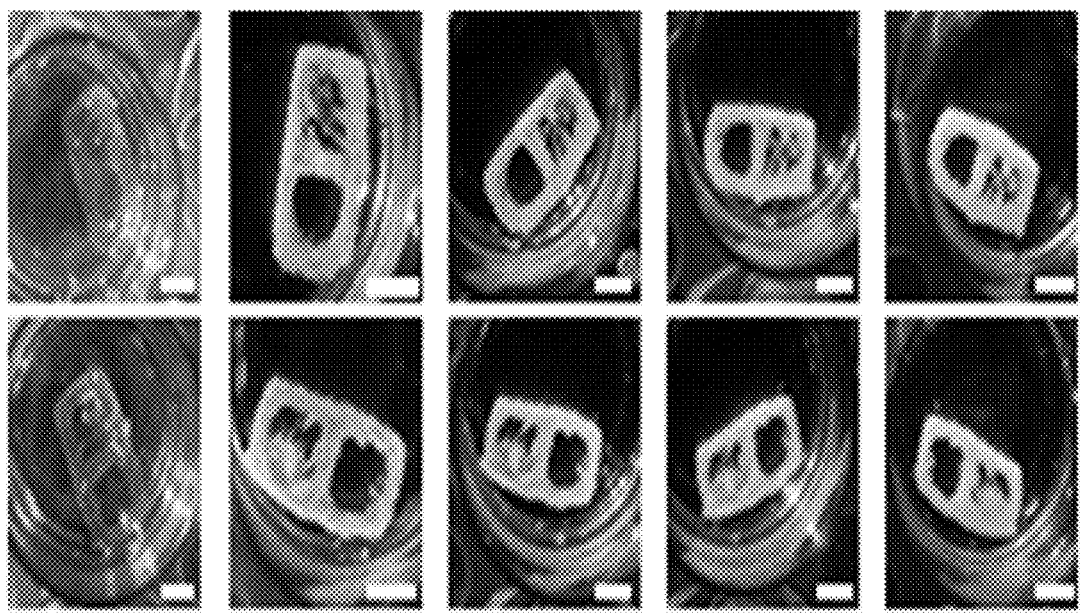

As an observation result, as shown in FIG. 11B, in the case of the unassembled macrostructure and block A produced only with alginate, it was seen that the construct did not collapsed after 30 days. The alginate hydrogel may generally collapse (degraded) by the interchange between calcium ions in the hydrogel and monovalent cations (e.g., $Na^+$) in the medium. However, 2% (w/w) is determined as a concentration at which the alginate hydrogel does not collapse due to the cation exchanged with an external medium. This means that the properties of the assembled construct are able to be changed by controlling the concentration of alginate.

Figure 11C:
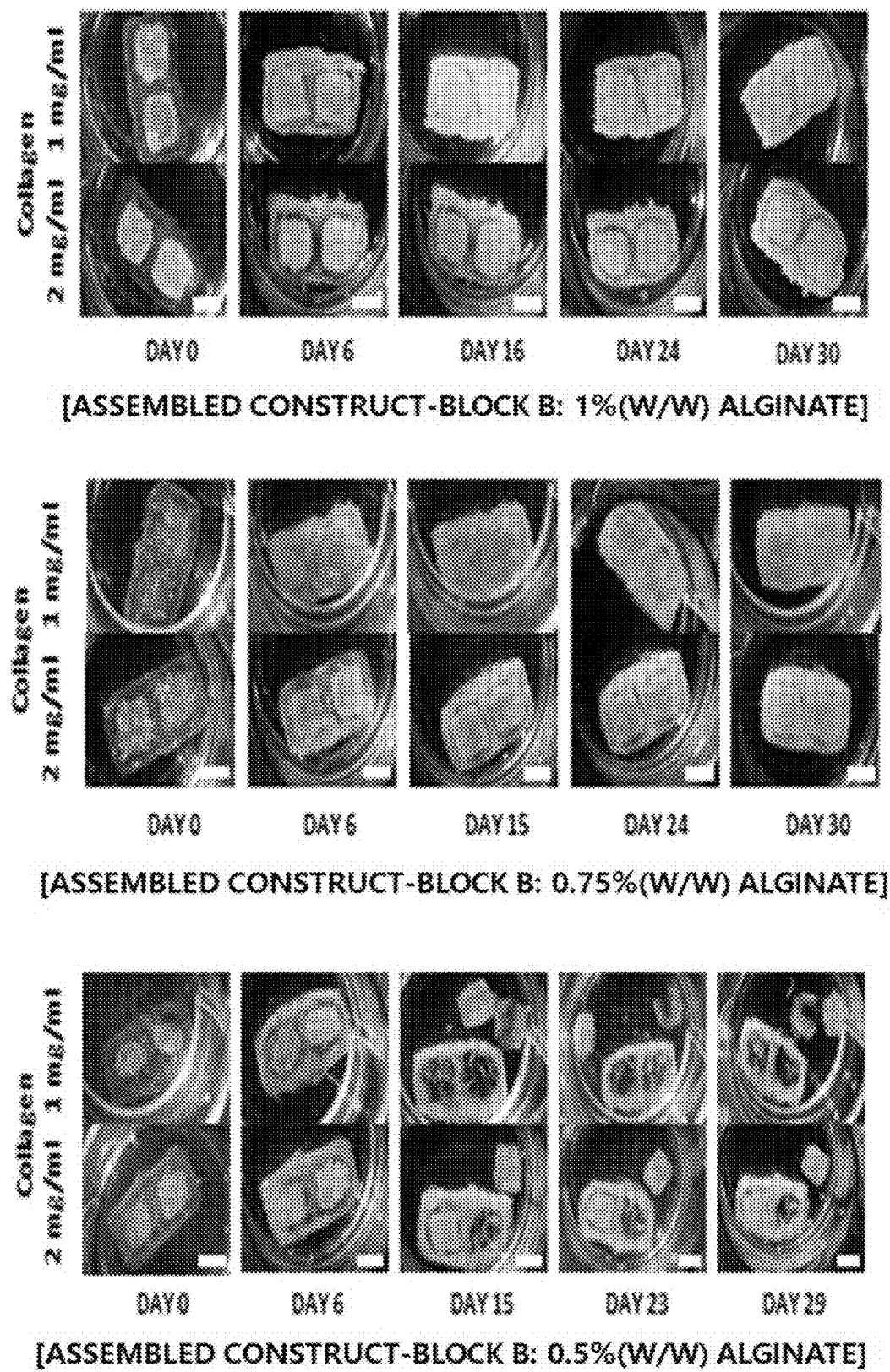
FIG. 11C shows the collapsed form of an assembled construct over time.

In the case of the assembled construct, as shown in FIG. 11C, it was confirmed that the lower the concentration of alginate in the block B, the faster the block B is separated from the block A. Specifically, when the alginate concentration was 0.5% (w/w), two weeks after the culture, the block B was separated from the block A, and when the alginate concentration was 0.75 or 1% (w/w), the shape of the assembled construct was maintained for 30 days or longer.

In addition, when the alginate concentration is 0.5% (w/w), it was confirmed that, as the collagen concentration decreases, a larger number of the block B is separated from the block A. It seems that, due to an excessively low alginate concentration in the block B, the collapse of the assembled structure caused by the cation exchange with a medium more easily occurs, and the lower the collagen concentration, the lower the physical properties of the blocks, and therefore, the block B is separated from the block A within a short period.

To reproduce the in vivo behavior of the collagen-containing construct, each construct was treated with collagenase. Specifically, the assembled construct was produced with the block B consisting of 1% (w/w) alginate and 1 or 2 mg/mL collagen, and treated with 1.2 U/well of collagenase.

Figure 12:
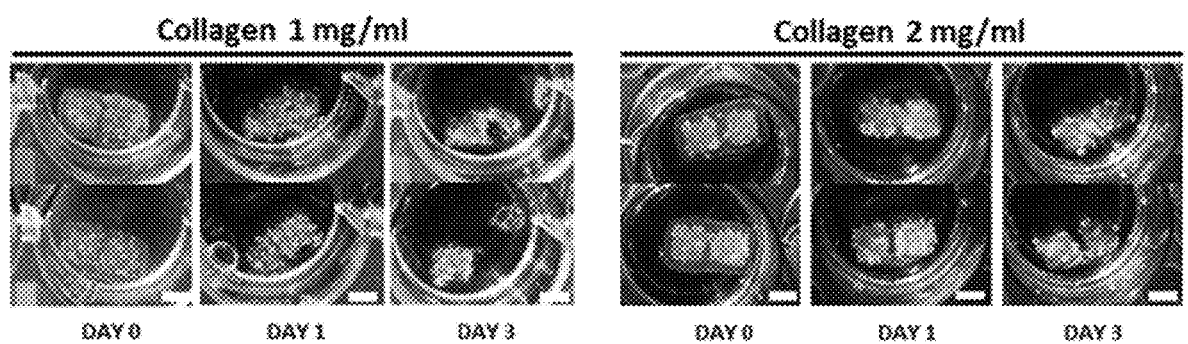
FIG. 12 shows the collapsed form of an assembled construct according to collagen treatment concentration.

As a result, as shown in FIG. 12, after three days, the assembled construct started to collapse, and as the collagen concentration decreased, the block B was more rapidly separated from the block A. According to this example, it was confirmed that, as the components or concentrations of the blocks are changed, the properties of the macrostructure are able to be changed.

Example 6: Comparison in Size of Produced Constructs According to Nozzle Size of Syringe 3D constructs were printed using a syringe with different nozzle sizes, and the specification accuracy of the printed constructs was confirmed. First, a cell-containing hydrogel precursor solution was prepared by adding pancreatic islets and pancreatic cells spheroid to a 2% (w/w) alginate solution. The hydrogel precursor solution was injected into a disposable syringe, and the syringe was mounted on a syringe holder. A 22 G (diameter: 410 μm) or 27 G (diameter: 210 μm) nozzle was connected to the syringe, and the syringe was fixed to a 3D bioprinter. A gelatin slush was fixed to a printing bed by the same method as described in Example 3-2, and then a cell-containing 3D construct was printed. The printed 3D construct was collected, the specifications of the cells and the construct were captured using a 40× magnification microscope, and the specifications of the construct was confirmed using an image analysis program. In the construct designed by AutoCAD, one width of a cuboid is 600 μm.

Figure 13:
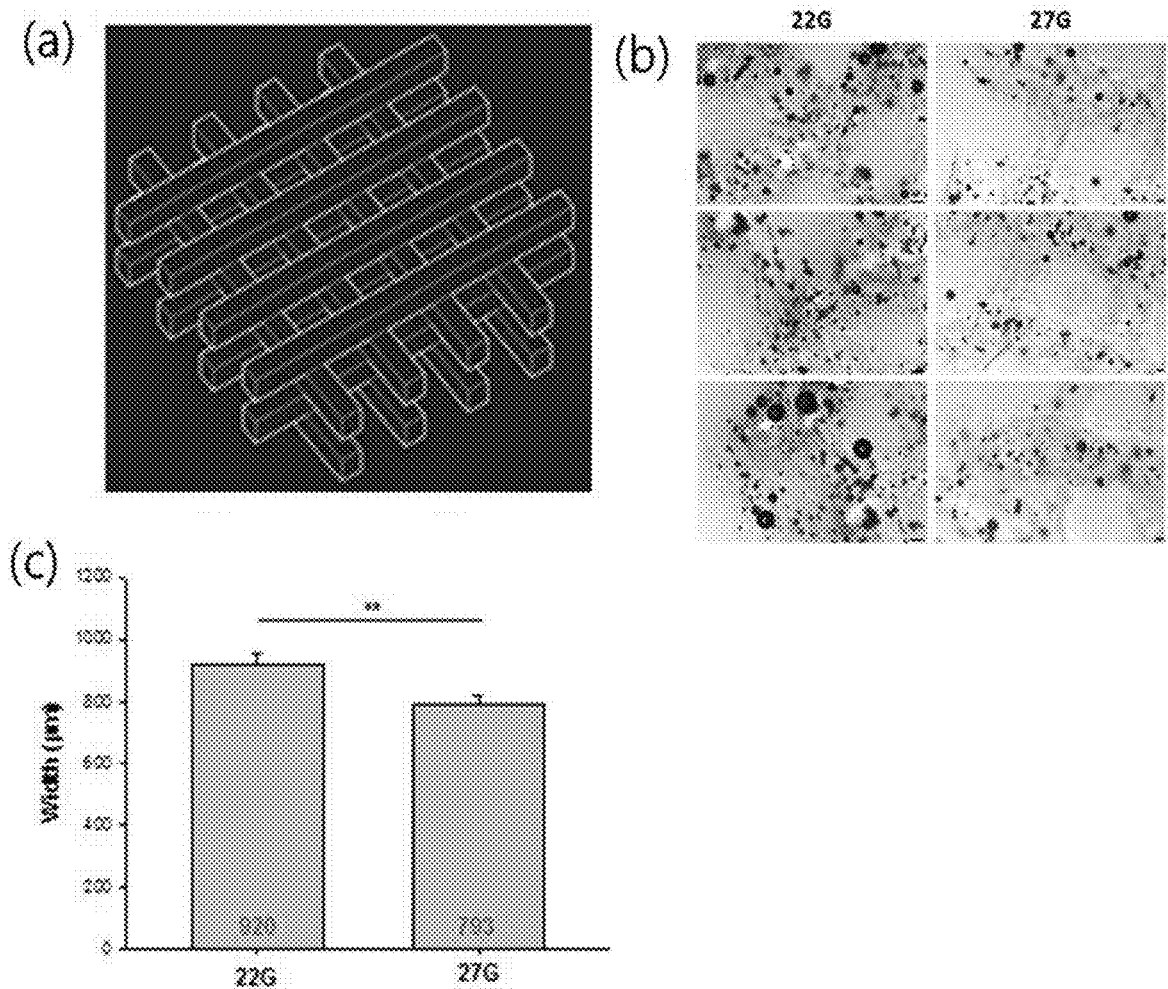
FIG. 13 shows (a) the shape of a 3D construct designed by AutoCAD, (b) the morphology of a construct printed using syringe nozzles with different sizes, and (c) the result of measuring absolute specifications of the printed structure.

As a result, as shown in FIG. 13(c), when a nozzle size is 27 G, an average width is 793 μm, and when a nozzle size is 22 G, an average width is 920 confirming that, as the nozzle size decreases, the specification of the 3D construct becomes accurate. However, when the nozzle size excessively decreases, cell viability can be drastically reduced due to high shear stress at the end of the nozzle. Therefore, the nozzle size was determined to be 27 G (210 μm), which is slightly larger than the diameter of a cell.

Example 7: Evaluation of Cell Viability Printed as 3D Construct

A hydrogel precursor solution containing cells was prepared by adding a pancreatic cells spheroid ($1.5 \times 10^5$ cells) to a 2% (w/w) alginate solution. The cell-containing alginate solution was injected into a disposable syringe, and the syringe was mounted on a syringe holder. After a 27 G (210 μm) nozzle was connected to the syringe, the syringe was fixed in a 3D bioprinter. A cell-containing 3D construct was printed and collected by the same method as described in Example 3-2 under optimized conditions, and after printing, the construct was incubated for 1 hour. Subsequently, the cell-containing 3D construct was stored in a 100 mM ethylenediaminetetraacetic acid disodium salt dihydrate (EDTA) solution (dissolved in HEPES buffer) for 7 minutes, and the alginate hydrogel was artificially degraded, followed by recovery of the cells. Pancreatic cells spheroid spheroid (control) which did not undergo 3D bioprinting or cells (experimental group) recovered after 3D bioprinting were dispensed into a 48-well plate. A medium was dispensed into each well where the cells were dispensed, treated with a CCK-8 drug at a concentration 1/10 of the medium volume, and then incubated for 4 hours. After 4 hours, absorbance was measured at 450 nm.

After the measurement of absorbance, the cells dispensed into each well were recovered, treated with 600 μL of RIPA buffer (cell lysis buffer), and then disrupted using a sonicator (22% amplitude, 3 sec ON, 4 sec OFF) for 17 seconds. Afterward, the cell debris was diluted with TE buffer included in a DNA assay kit (Invitrogen), and a PICOGREEN solution reacting with DNA was added thereto, followed by measurement of a fluorescence value in a wavelength range of 480 to 530 nm.

Figure 14A:
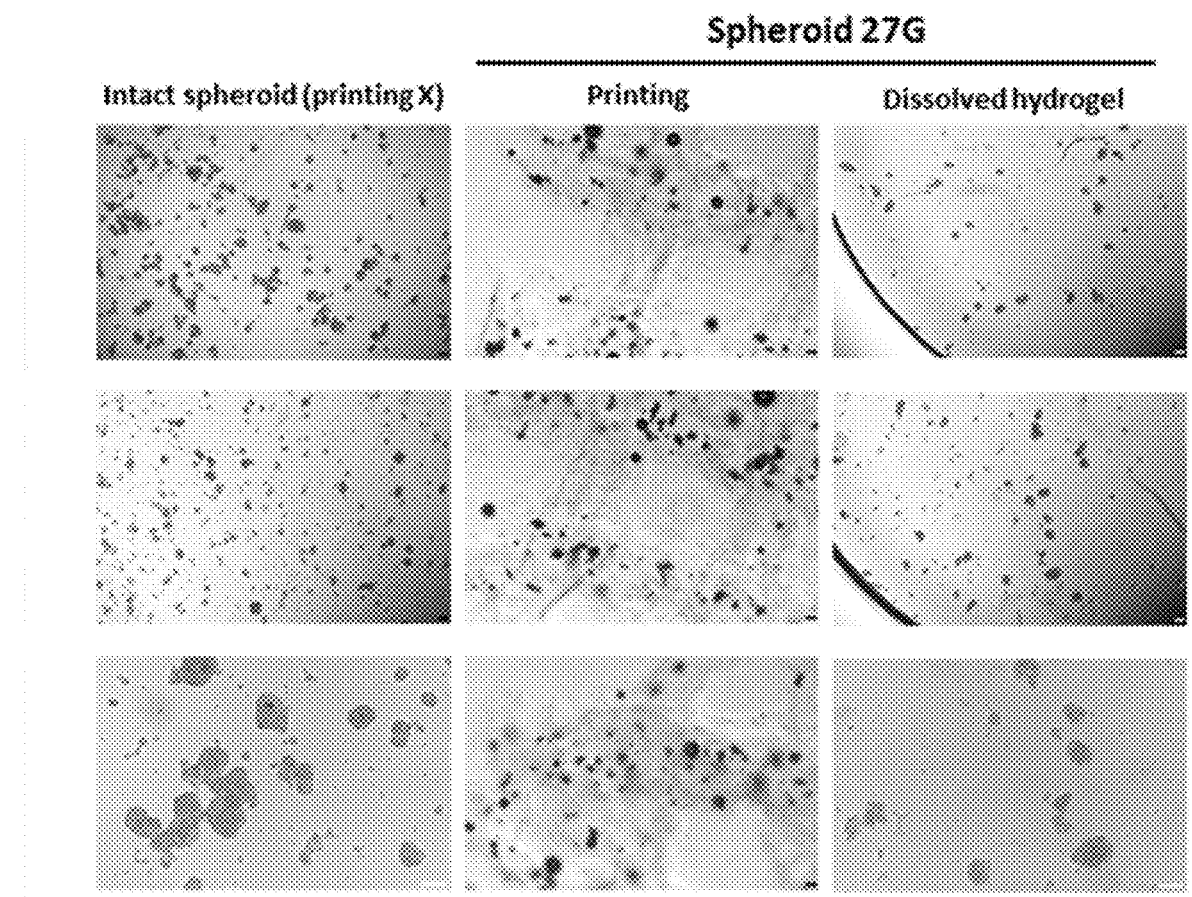
FIG. 14A shows the morphology of cells contained in a 3D construct printed with a 27 G syringe nozzle.
Figure 14B:
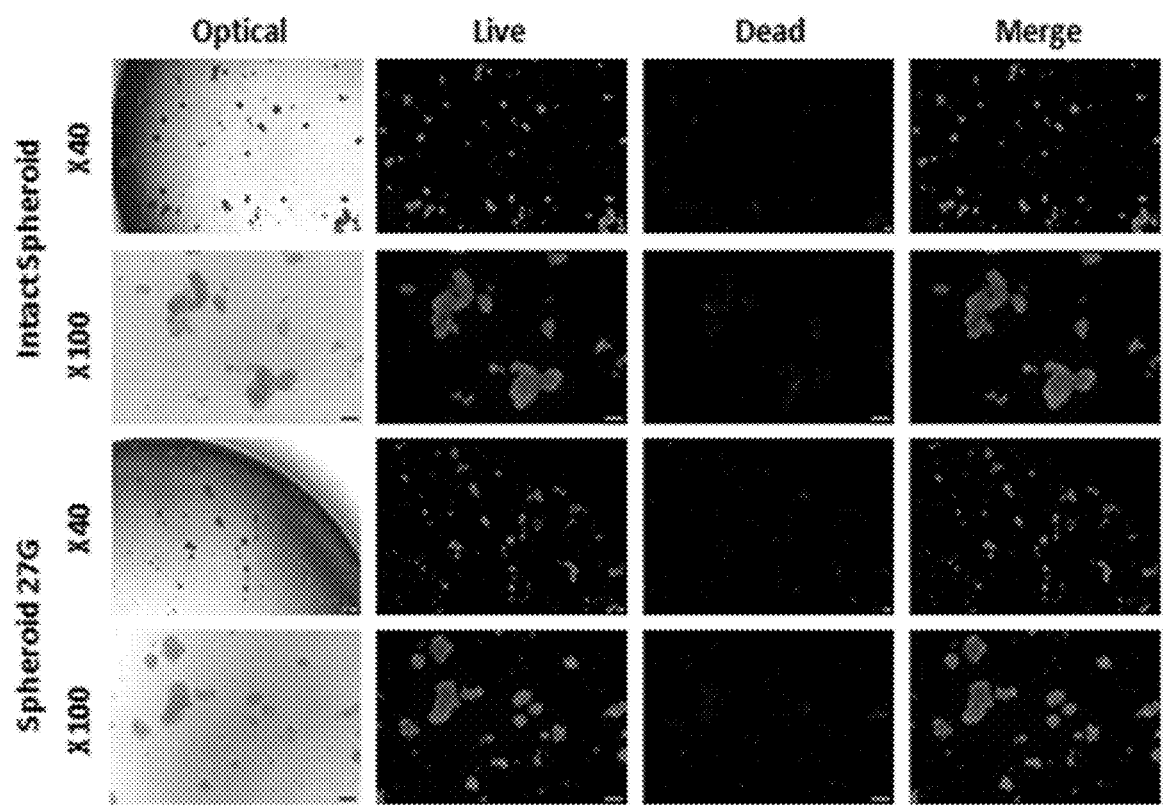
FIG. 14B are images of the cells contained in a 3D construct printed with a 27 G syringe nozzle, which are obtained using a fluorescence microscope.
Figure 14C:
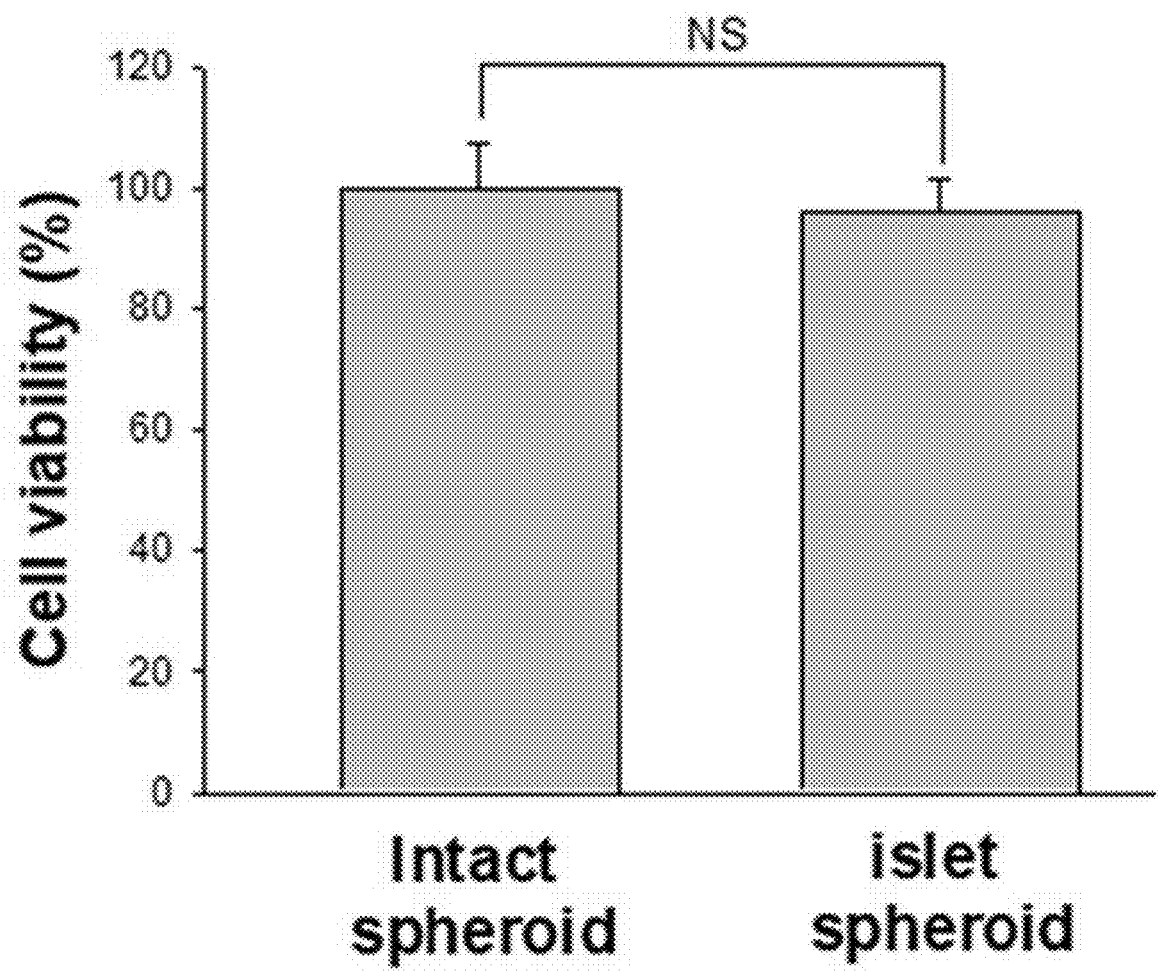
FIG. 14C shows the result of the viability of the cells contained in a 3D construct printed with a 27 G syringe nozzle.

As a correction result obtained by dividing the absorbance measured in the CCK-8 experiment by the fluorescence value, as shown in FIG. 14B, there was no significant difference in cell viability between a control and an experimental group. This means that the printing process with a 27 G (210 μm)-sized nozzle does not significantly affect cell viability.

In addition, a Live/Dead assay (Sigma-Aldrich) was performed to qualitatively evaluate cell viability. Calcein-AM (live cell) and ethidium homodimer-1 (dead cell) were added to wells of a 48-well plate at a concentration of 1 μM and then incubated for 15 minutes. Afterward, green fluorescence (live cell) and red fluorescence (dead cell) were observed.

As a result, it was confirmed that, in both of the control and the experimental group, red fluorescence is expressed at a significantly lower level than green fluorescence, indicating that cell viability is not significantly affected in the process of producing a cell-containing construct.

Example 8: Production of Various Shapes of Blocks Containing Cells

Since cell viability is not significantly affected by the conditions optimized by the previous experiment (printing speed 12 mm/s, input flow 60%, filling density 70%) and the printing process, various shapes of 3D constructs containing cells were produced. Specifically, cuboid blocks having 0, 1, 4 and 9 holes were designed, and 3D constructs were printed by the same method as described in Example 8 using a 2% (w/w) alginate solution and pancreatic cell spheroid. The printed 3D construct was collected by the same method as described in Example 2-2.

Figure 15:
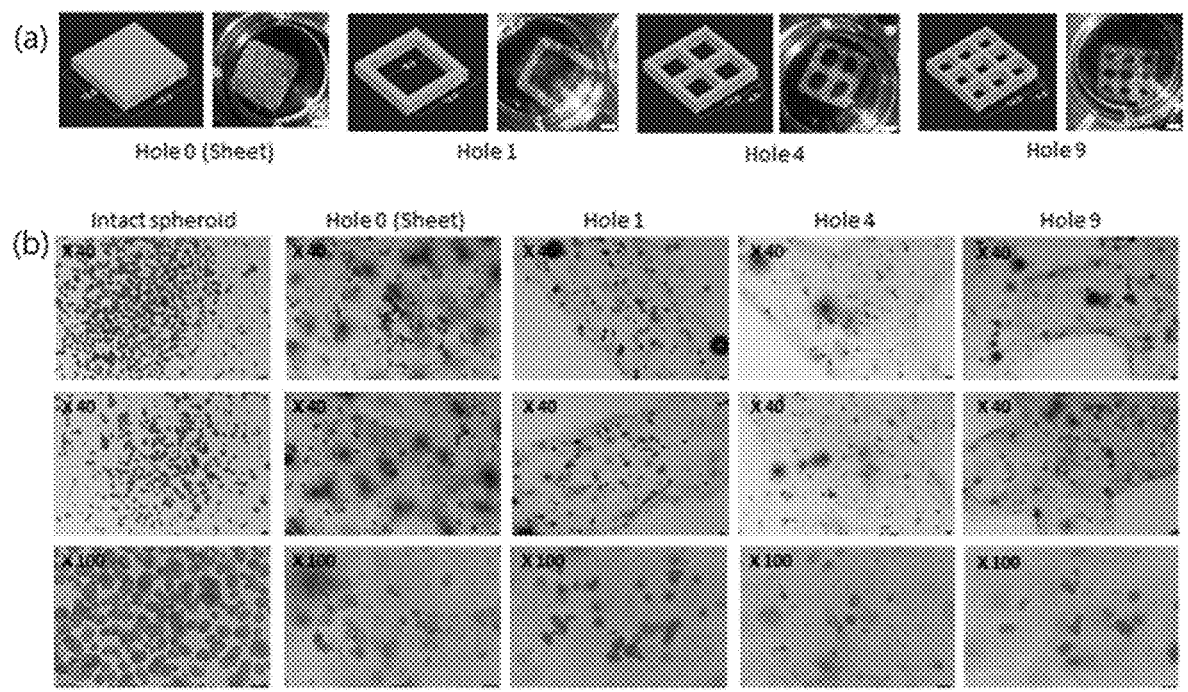
FIG. 15 shows (a) the shapes of 3D constructs formed with multiple holes and (b) the morphology of cells contained in the printed 3D construct.

The shape of the 3D construct and the morphology of cells encapsulated therein were observed using an optical microscope. As a result, as shown in FIG. 15(b), it was confirmed that cells are uniformly distributed in the blocks regardless of the shape of a block, and it can be seen that the morphology of cells in the experimental groups (0, 1, 4 and 9 holes) was also superior to that of the control (cells not subjected to bioprinting, intact spheroid). The shapes of the printed blocks were also similar to the designed shapes, indicating that various shapes of blocks containing cells can be produced by 3D bioprinting.

Example 9: Degree of Hypoxia of Cells According to Shape of 3D Construct

A cell-containing block was printed using a 27 G nozzle, and the extent to which hypoxia occurs was evaluated by measuring ROS (reactive oxygen species) generated in the cells contained in the block.

Specifically, 3D constructs were designed to have cuboid (6 mm×6 mm×2 mm) and square donut (6 mm×6 mm×2 mm, inner empty space 4.8 mm×4.8 mm×2 mm), and then printed to contain pancreatic cells spheroid ($1.5 \times 10^5$ cells) by the same method as described in Example 7.

Pancreatic cells spheroid (control; intact spheroid) which did not undergo 3D bioprinting, the cuboid-shaped cell-containing construct (Experimental Group 1; hole 0) and the square donut-shaped cell-containing construct (Experimental Group 2; hole 1) were dispensed into a 48-well plate. To induce hypoxia, each sample was incubated for 24 hours, a 10 μM dichlorodihydrofluorescein diacetate ($H_2DCFDA$) solution (dissolved in HEPES buffer) was added to each sample, followed by incubation for 30 minutes. Subsequently, the $H_2DCFDA$ solution was removed, a medium was added to each sample, and fluorescence was measured in a wavelength range of 485 to 530 nm. The shape of cells encapsulated in the 3D construct and $H_2DCFDA$ fluorescence were observed using a confocal microscope.

Figure 16A:
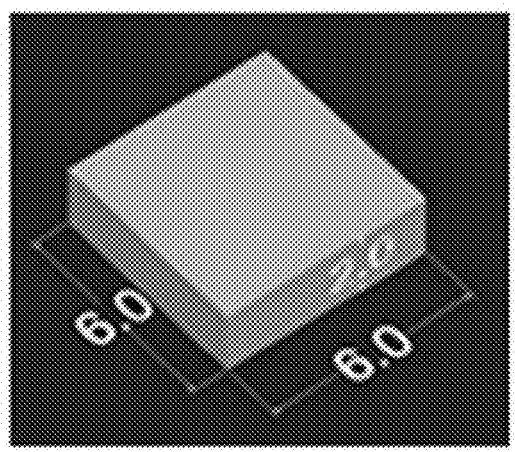
FIG. 16A shows the shape of a 3D construct designed to evaluate hypoxia in cells.
Figure 16A:
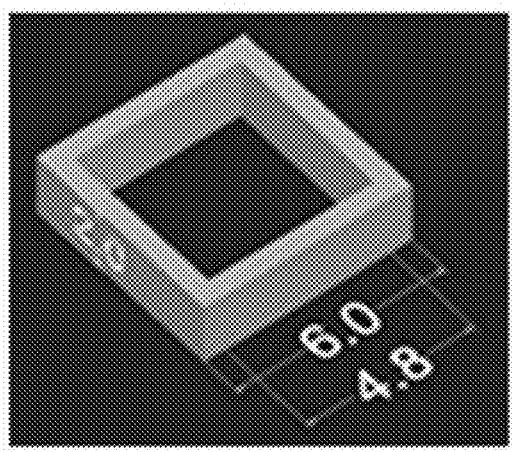
Figure 16B:
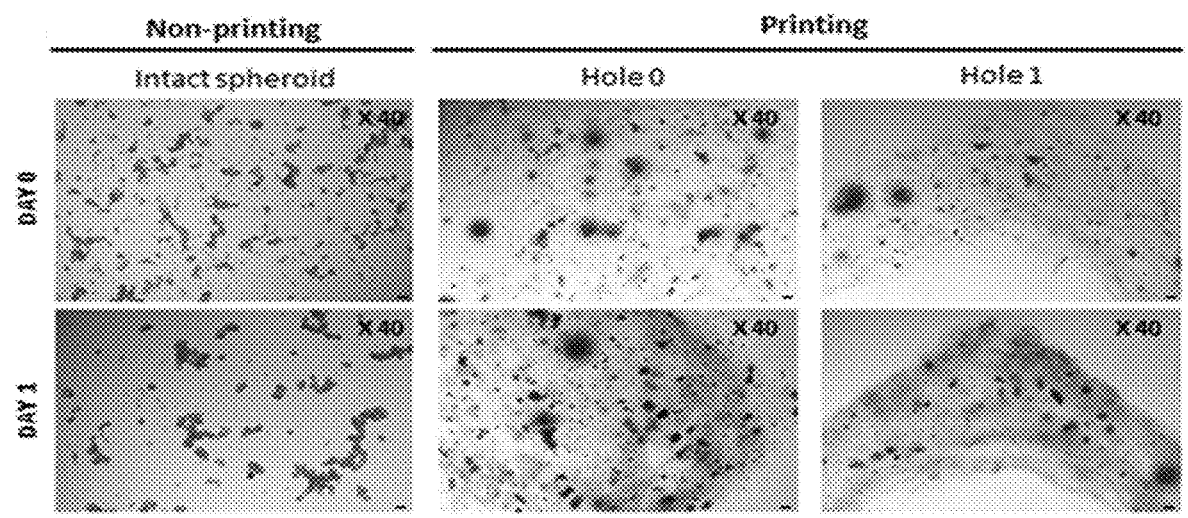
FIG. 16B shows the result of confirming the morphology of cells contained in the printed 3D construct.
Figure 16C:
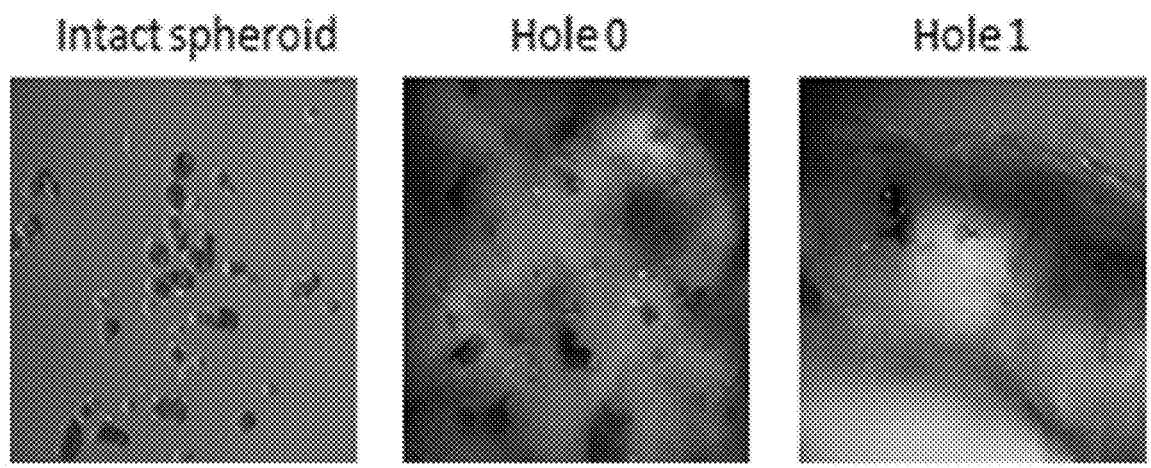
FIGS. 16C and 16D show the level of reactive oxygen species (ROC) production in cells contained in the printed 3D construct.
Figure 16D:
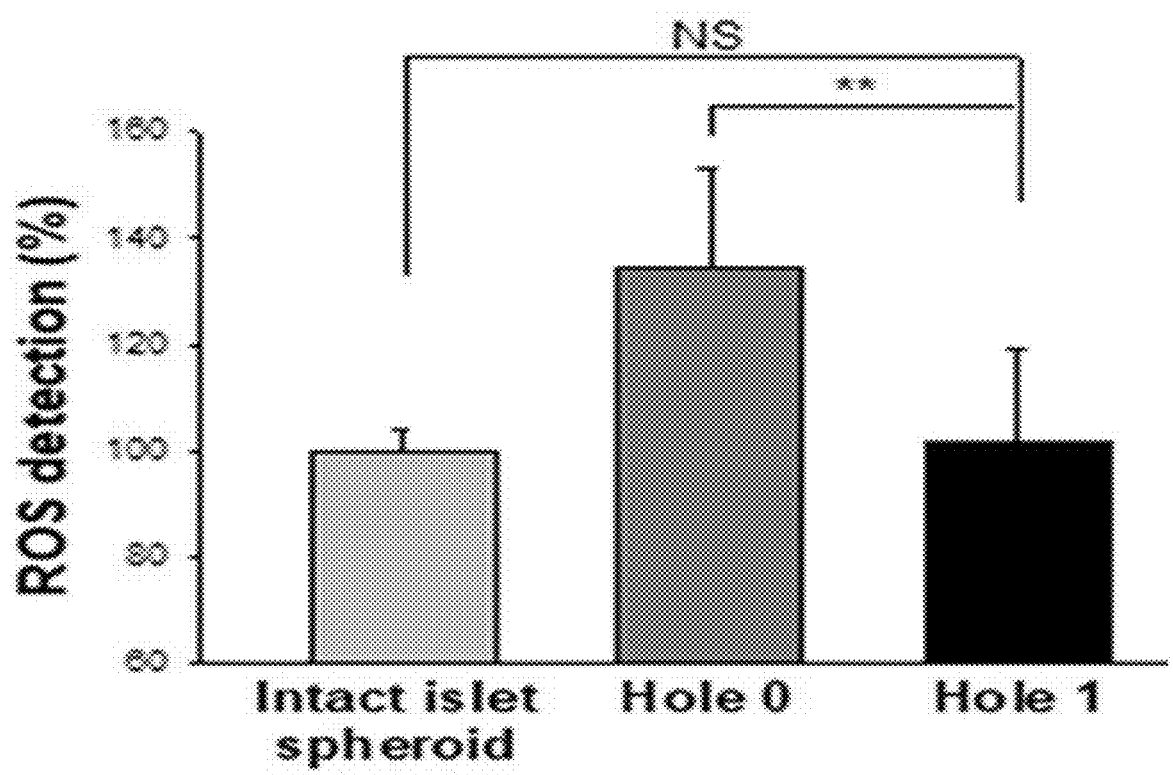

As a result, as shown in FIGS. 16C and 16D, comparing the control and Experimental Group 2, it was seen that the fluorescence of Experimental Group 1 is significantly high. There was no significant difference in fluorescence value between the control and Experimental Group 2. Therefore, in a 3D construct with no inner space, more ROS are generated in cells, confirming that hypoxia more actively occurs.

Example 10: Transplantation of Cell-Containing 3D Construct 10-1. Xenotransplantation of 3D Construct An unassembled construct (control), block A (single block) and an assembled construct (block A+block B) were formed, and incubated before transplantation. The unassembled construct and the block A used a 2% (w/w) alginate solution, and the block B was formed of a mixed solution (1:1) of 2% (w/w) alginate and collagen (1 mg/mL). Cells were pancreatic islets isolated from a rat.

Three 8 week-old nude mice were anesthetized, and each of the unassembled construct (control), the block A and the assembled construct was subcutaneously transplanted into the dorsal region. Thirty days after transplantation, dorsal tissue containing the transplanted construct was collected, and the engraftment of the construct was confirmed.

Figure 17:
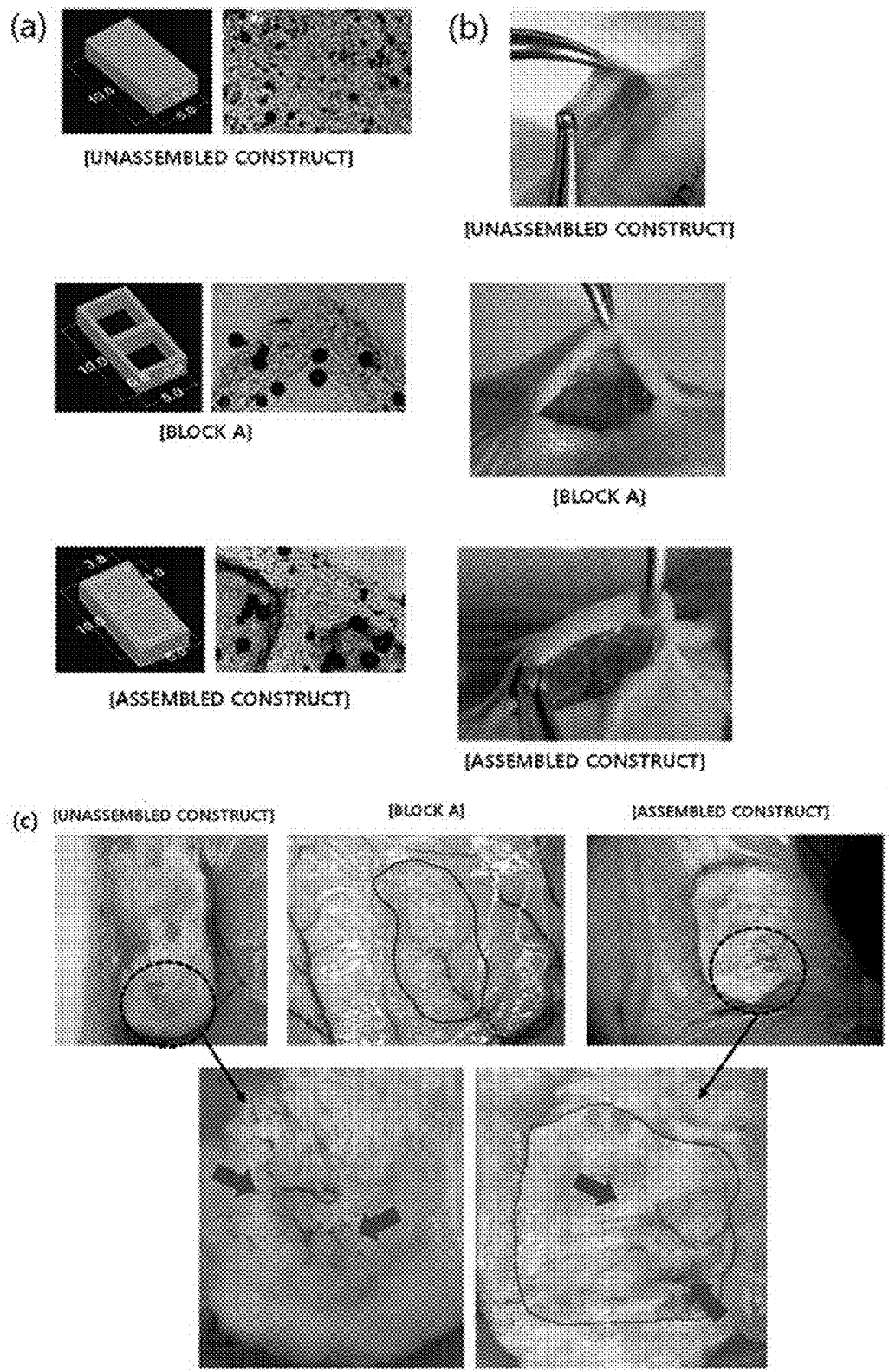
FIG. 17 shows (a) the shape of a 3D construct to implant into a nude mouse, (b) the shape of a 3D construct implanted into a nude mouse, and (c) the shape of a 3D construct observed 30 days after implantation.

As a result, as shown in FIG. 17B, it can be seen that, when the block A was transplanted, the alginate hydrogel collapses such that the original shape of the construct is not maintained. It seems that this is because the mechanical properties are weak since the block A is a single block which is not assembled. Meanwhile, the control maintained the original shape since the mechanical properties are superior to the single block, and as shown in FIG. 17C, it was confirmed that blood vessels are formed around the construct from the dorsal region. When the assembled construct is transplanted, a similar tendency to the control is shown, confirming that the construct is engrafted into the dorsal region, and the assembly boundary between the block A and the block B was also confirmed.

Through the experimental result, it was confirmed that the original shape can be maintained even when the construct formed by assembly is transplanted in vivo.

10-2. Tissue analysis of transplanted 3D construct

To evaluate the extent of engraftment of the transplanted 3D construct, dorsal tissue containing the construct isolated in Example 10-1 was subjected to immunohistochemistry (IHC) and hematoxylin & eosin (H&E) staining.

The isolated dorsal tissue was stored in a Karnovsky fixation solution for 2 days, and the sufficiently fixed dorsal tissue was washed to remove the fixation solution. Subsequently, the dorsal tissue was sequentially immersed in 70, 80, 90 and 100% ethanol for rehydration, and a paraffin block was prepared. The paraffin block was cut to a thickness of 6 μm, and the cut tissue section was attached to a slide glass. Afterward, the slide glass was stored in a 60° C. oven for 30 minutes, and then immersed in xylene to remove the paraffin. The slide glass was sequentially immersed in 100, 90, 80 and 70% ethanol for hydration, and the tissue section was stained with a H&E solution. To remove the staining solution around the dorsal tissue, the slide glass was sequentially washed with 70, 80, 90 and 100% ethanol. A mounting solution was dropped on the proximity of the stained dorsal tissue section, and then covered with a cover glass to protect the stained tissue section.

Figure 18:
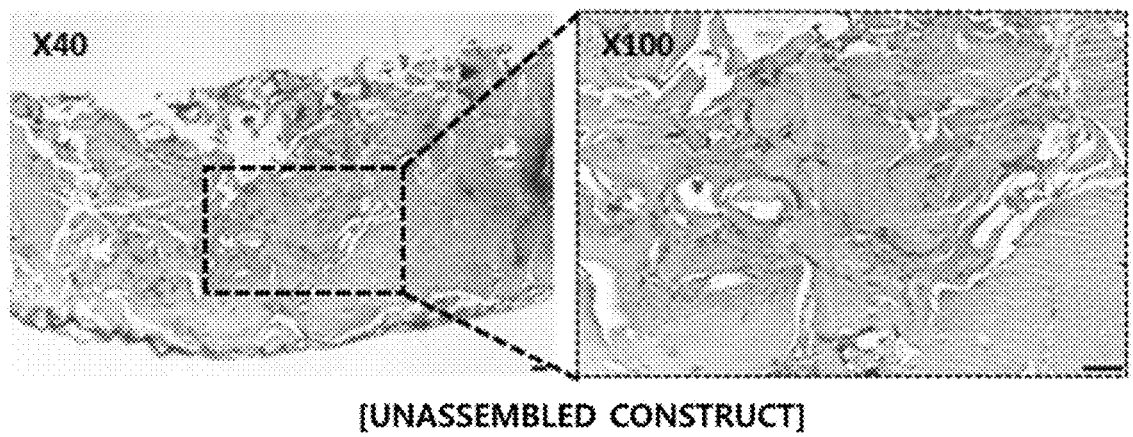
FIG. 18 shows the result of staining mouse tissue containing an implanted 3D construct with a hematoxylin & eosin solution, after being isolated.
Figure 18:
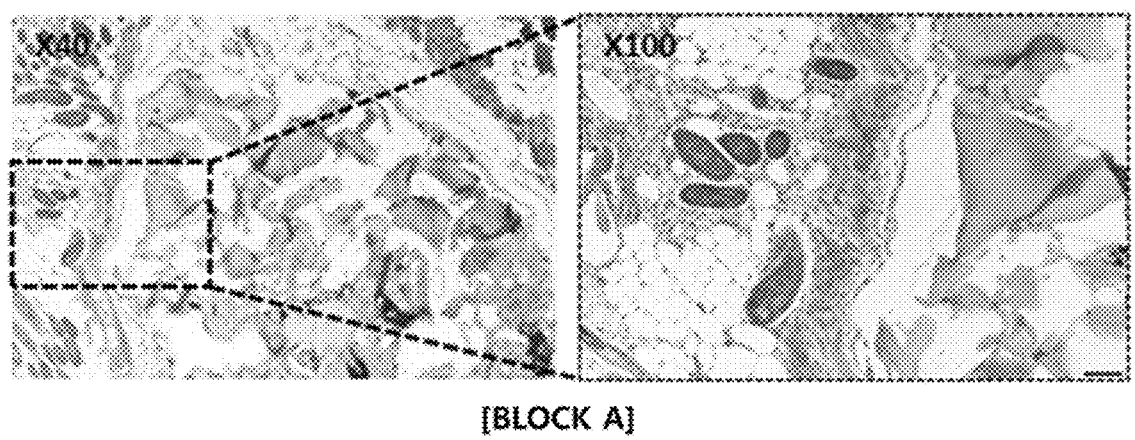
Figure 18:
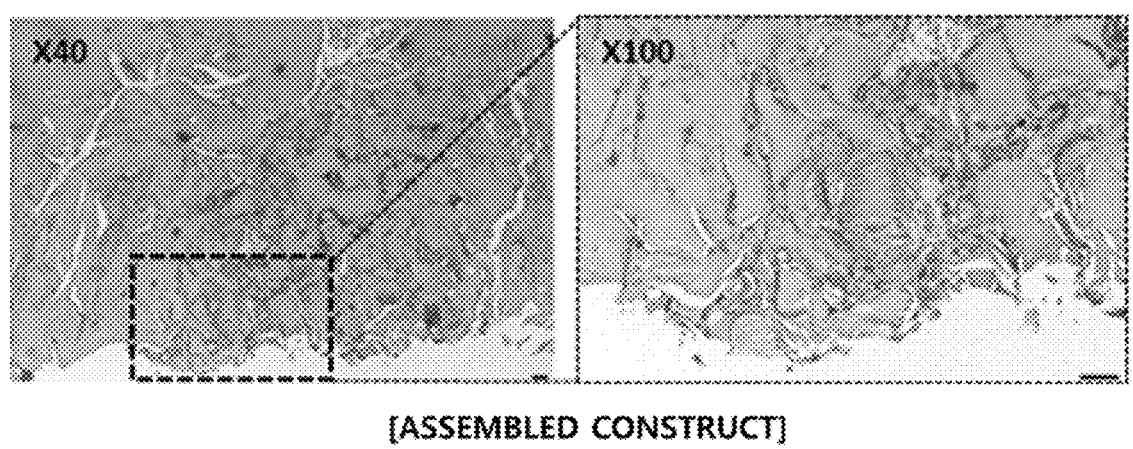

As a result of the H&E staining, as shown in FIG. 18, when the unassembled construct or the assembled construct is transplanted, the original shape of each construct is maintained, nude mouse tissue (native tissue) formed in the transplanted construct and nude mouse cells (migrated native cells) migrated into the construct were able to be confirmed. However, when the block A is transplanted, the shape of the construct was not maintained, and it was observed that the construct was not broken into small pieces. Such a result is similar to that of Example 11-1, and the shape of the block A is not maintained due to poor physical properties, compared with other constructs.

IHC was performed as follows. Paraffin was removed by the same method described above, and the tissue section was sequentially immersed in 100, 90, 80 and 70% ethanol for hydration. Subsequently, for antigen retrieval from the hydrated tissue, a slide glass was stored in a 60° C. sodium citrate solution (pH 6.0) for 30 minutes. The sodium citrate solution on the slide glass was removed with PBS-Tween 20 (PBS-T). The tissue section was treated with 20% goat serum diluted in PBS-T for 30-minute to 1-hour blocking. A primary antibody, an anti-CD34 antibody, was diluted in 20% goat serum at 1:100, and then the tissue section was treated and reacted with the primary antibody overnight at 4° C. The CD34 antibody is used to stain blood vessels formed by engraftment of a transplanted construct into the tissue of a nude mouse.

Next day, the slide glass was washed with PBS to remove the primary antibody and the goat serum. A secondary antibody (goat-anti rat) was diluted in PBS at 1:100, and then the slide glass was treated with the secondary antibody and stored for 60 minutes at room temperature. Afterward, a DAPI (4',6-diamidino-2-phenylindole) mounting solution was dropped on the slide glass, and covered with a cover glass to protect the stained tissue from the outside. After staining, stained tissues were observed using optical and fluorescence microscopes.

Figure 19:
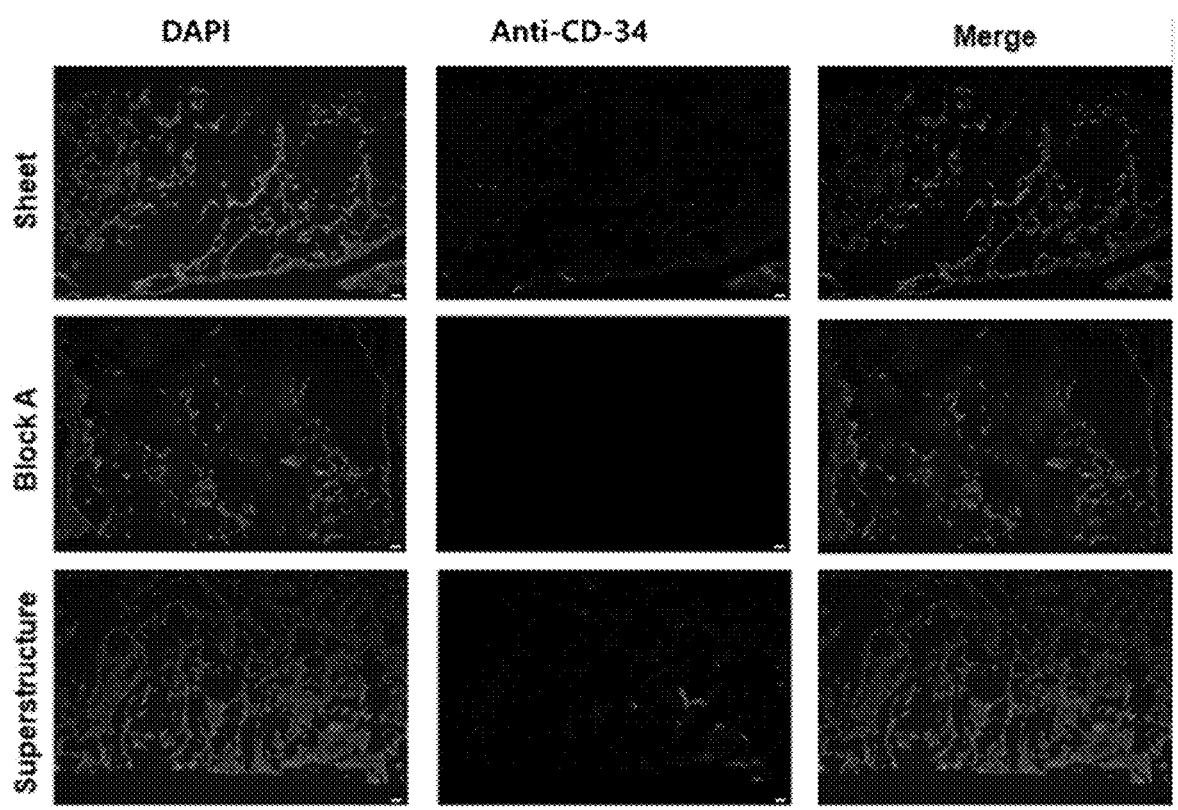
FIG. 19 shows the result of staining mouse tissue containing an implanted 3D construct with a CD34 antibody.

As a result of the IHC staining, as shown in FIG. 19, compared with when the block A was transplanted, when the unassembled construct or assembled construct was transplanted, a strong CD34 fluorescent signal was observed. Particularly, it was seen that in the case of the assembled construct, a stronger fluorescent signal is observed in the block B containing collagen.

Through this experiment, it was confirmed that, even when a construct formed by assembling different blocks is transplanted, the shape of the construct may be maintained, and the properties of the construct may be changed by changing the components of a block.

In the above, the present invention was described with reference to examples. It will be understood by those of ordinary skill in the art that the present invention can be implemented in modified forms without departing from the essential features of the present invention. Therefore, the disclosed embodiments should be considered in a descriptive aspect, rather than a limiting aspect. The scope of the present invention is shown in the claims rather than the foregoing description, and all differences within the equivalent range thereto will be construed as being included in the present invention.

The invention claimed is:

1. A three-dimensional (3D) hydrogel scaffold, comprising:
    a first hydrogel block containing cells to be implanted in vivo; and
    a second hydrogel block,
    wherein the first hydrogel block or second hydrogel block has a hole,
    wherein the first hydrogel block and the second hydrogel block are assembled together through the hole, and have different biodegradabilities.

2. The 3D hydrogel scaffold of claim 1, wherein the hole is formed through the first hydrogel block or second hydrogel block.

3. The 3D hydrogel scaffold of claim 1, wherein each or both of the first hydrogel block and the second hydrogel block further contain a growth factor.

4. The 3D hydrogel scaffold of claim 3, wherein the growth factor is selected from the group consisting of an epidermal growth factor (EGF), a fibroblast growth factor (FGF), a transforming growth factor β (TGFβ), a platelet-derived growth factor (PDGF), a vascular endothelial growth factor (VEGF), an insulin-like growth factor 1 (IGF-1), thioredoxin (TRX), a stem cell factor (SCF), a hepatocyte growth factor (HGF), a human growth hormone (HGH), and angiogenin, and a combination thereof.

5. The 3D hydrogel scaffold of claim 1, wherein each or both of the first hydrogel block and the second hydrogel block are formed in a donut shape.

6. The 3D hydrogel scaffold of claim 1, wherein each or both of the first hydrogel block and the second hydrogel block is formed in a lattice shape.

7. A method of producing a 3D hydrogel scaffold of claim 1, comprising:
   forming a first hydrogel block by printing a mixture of a biodegradable first hydrogel solution and cells by 3D bioprinting;
   forming a second hydrogel block by printing a biodegradable second hydrogel solution by 3D bioprinting; and
   assembling the first hydrogel block and the second hydrogel block,
   wherein the first hydrogel block or second hydrogel block has a hole; and
   wherein the first hydrogel block and the second hydrogel block are assembled together through the hole.

8. The method of claim 7, wherein the first hydrogel solution and the second hydrogel solution are solutions in which one or more polymers selected from alginate, heparin, hyaluronic acid, collagen and gelatin are dissolved, and have different polymer components or concentrations.

9. The method of claim 7, wherein the first hydrogel solution is an alginate solution, and the second hydrogel solution is a mixed solution of alginate and collagen.

10. The method of claim 7, wherein the hole is formed through the first hydrogel block or second hydrogel block.

11. The method of claim 7, wherein the printing by the 3D bioprinting is performed under conditions of a printing speed of 5 to 20 mm/s, an input flow of 50 to 100% and a filling density of 50 to 100%.

* * * * *